US008653209B2

(12) United States Patent
Brant et al.

(10) Patent No.: US 8,653,209 B2
(45) Date of Patent: *Feb. 18, 2014

(54) HIGH VINYL TERMINATED PROPYLENE BASED OLIGOMERS

(71) Applicant: ExxonMobil Chemical Patents Inc., Baytown, TX (US)

(72) Inventors: Patrick Brant, Seabrook, TX (US); Donna J. Crowther, Seabrook, TX (US); Andrew G. Narvaez, Jr., Pasadena, TX (US)

(73) Assignee: ExxonMobil Chemical Patents Inc., Houston, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 13/670,085

(22) Filed: Nov. 6, 2012

(65) Prior Publication Data

US 2013/0066103 A1  Mar. 14, 2013

Related U.S. Application Data

(62) Division of application No. 12/143,663, filed on Jun. 20, 2008, now Pat. No. 8,372,930.

(51) Int. Cl.
*C08F 4/64* (2006.01)
*C08F 4/52* (2006.01)
*C08F 4/76* (2006.01)
*C08F 10/06* (2006.01)

(52) U.S. Cl.
USPC ........... 526/160; 526/170; 526/941; 526/943; 526/351; 526/352; 526/901

(58) Field of Classification Search
USPC .................................. 526/348, 351, 160, 170
See application file for complete search history.

(56) References Cited

U.S. PATENT DOCUMENTS

| | | | |
|---|---|---|---|
| 3,022,305 A | 2/1962 | Carboni | |
| 3,235,484 A | 2/1966 | Colfer | |
| 3,382,291 A | 5/1968 | Brennan | |
| 3,742,082 A | 6/1973 | Brennan | |
| 3,769,363 A | 10/1973 | Brennan | |
| 3,780,128 A | 12/1973 | Shubkin | |
| 3,876,720 A | 4/1975 | Heilman et al. | |
| 4,069,023 A | 1/1978 | Brois et al. | |
| 4,110,377 A | 8/1978 | Clerici et al. | |
| 4,172,855 A | 10/1979 | Shubkin et al. | |
| 4,197,398 A | 4/1980 | Floyd et al. | |
| 4,239,930 A | 12/1980 | Allphin et al. | |
| 4,367,352 A | 1/1983 | Watts, Jr. et al. | |
| 4,413,156 A | 11/1983 | Watts, Jr. et al. | |
| 4,568,663 A | 2/1986 | Mauldin | |
| 4,619,756 A | 10/1986 | Dickakian | |
| 4,619,758 A | 10/1986 | Pratt et al. | |
| 4,704,491 A | 11/1987 | Tsutsui et al. | |
| 4,814,540 A * | 3/1989 | Watanabe et al. | 585/523 |
| 4,827,064 A | 5/1989 | Wu | |
| 4,827,073 A | 5/1989 | Wu | |
| 4,910,355 A | 3/1990 | Shubkin et al. | |
| 4,914,254 A | 4/1990 | Pelrine | |
| 4,926,004 A | 5/1990 | Pelrine et al. | |
| 4,956,122 A | 9/1990 | Watts et al. | |
| 4,967,032 A | 10/1990 | Ho | |
| 4,973,414 A | 11/1990 | Nerger et al. | |
| 4,988,764 A | 1/1991 | Nishio et al. | |
| 4,999,403 A | 3/1991 | Datta et al. | |
| 5,026,948 A | 6/1991 | Forbus | |
| 5,068,487 A | 11/1991 | Theriot | |
| 5,087,788 A | 2/1992 | Wu | |
| 5,145,819 A | 9/1992 | Winter et al. | |
| 5,171,919 A * | 12/1992 | Watanabe et al. | 585/523 |
| 5,211,834 A | 5/1993 | Forester | |

(Continued)

FOREIGN PATENT DOCUMENTS

| | | | |
|---|---|---|---|
| CN | 101011062 | 8/2007 | |
| EP | 0 283 958 | 9/1988 | |
| EP | 0 485 822 | 5/1992 | |
| EP | 0 485 823 | 5/1992 | |
| EP | 608 707 A1 * | 1/1994 | C07C 2/34 |
| EP | 0 604 917 | 7/1994 | |
| EP | 0 613 873 | 7/1994 | |
| EP | 0 619 325 | 10/1994 | |
| EP | 0 719 802 | 7/1996 | |
| EP | 0 767 182 | 4/1997 | |
| EP | 0 802 216 | 10/1997 | |
| EP | 0 958 309 | 11/1999 | |
| EP | 1 361 232 | 11/2003 | |
| EP | 1 849 757 | 10/2007 | |
| EP | 1 862 491 | 12/2007 | |

(Continued)

OTHER PUBLICATIONS

Balboni et al., $C_2$-*Symmetric Zirconocenes for High Molecular Weight Amorphous Poly(propylene)*, Macromolecular Chemistry and Physics, 2001, vol. 202, No. 10, pp. 2010-2028.

(Continued)

*Primary Examiner* — Rip A Lee
(74) *Attorney, Agent, or Firm* — Catherine L. Bell

(57) ABSTRACT

This invention relates to a co-oligomer having an Mn of 300 to 30,000 g/mol comprising 10 to 90 mol % propylene and 10 to 90 mol % of ethylene, wherein the oligomer has at least X % allyl chain ends, where: 1) X=(−0.94(mole % ethylene incorporated)+100), when 10 to 60 mole % ethylene is present in the co-oligomer, and 2) X=45, when greater than 60 and less than 70 mole % ethylene is present in the co-oligomer, and 3) X=(1.83*(mole % ethylene incorporated)−83), when 70 to 90 mole % ethylene is present in the co-oligomer. This invention also relates to a homo-oligomer, comprising propylene, wherein the oligomer has: at least 93% allyl chain ends, an Mn of about 500 to about 20,000 g/mol, an isobutyl chain end to allylic vinyl group ratio of 0.8:1 to 1.2:1.0, and less than 100 ppm aluminum. This invention also relates to a process of making homo-oligomer, comprising propylene, wherein the productivity is greater than 4500 g/mmol Hf (or Zr)/hour.

49 Claims, 2 Drawing Sheets

(56) References Cited

U.S. PATENT DOCUMENTS

| | | | |
|---|---|---|---|
| 5,229,022 A | 7/1993 | Song et al. | |
| 5,241,025 A | 8/1993 | Hlatky et al. | |
| 5,252,677 A | 10/1993 | Tomita et al. | |
| 5,266,186 A | 11/1993 | Kaplan | |
| 5,321,189 A * | 6/1994 | Mueller et al. | 585/512 |
| 5,348,982 A | 9/1994 | Herboltzheimer et al. | |
| 5,350,817 A | 9/1994 | Winter et al. | |
| 5,382,634 A | 1/1995 | Koyama et al. | |
| 5,439,607 A | 8/1995 | Patil | |
| 5,504,171 A | 4/1996 | Etherton et al. | |
| 5,514,761 A | 5/1996 | Etherton et al. | |
| 5,545,674 A | 8/1996 | Behrmann et al. | |
| 5,616,153 A | 4/1997 | Mike et al. | |
| 5,625,106 A * | 4/1997 | Marks et al. | 585/512 |
| 5,670,595 A | 9/1997 | Meka et al. | |
| 5,679,811 A * | 10/1997 | Winter et al. | 556/7 |
| 5,688,887 A | 11/1997 | Bagheri et al. | |
| 5,696,045 A | 12/1997 | Winter et al. | |
| 5,741,946 A | 4/1998 | Wei | |
| 5,744,541 A | 4/1998 | Sawaguchi et al. | |
| 5,750,815 A | 5/1998 | Grubbs et al. | |
| 5,756,428 A | 5/1998 | Emert et al. | |
| 5,756,609 A | 5/1998 | Cohen | |
| 5,856,256 A | 1/1999 | Marks et al. | |
| 5,874,661 A | 2/1999 | Verrelst et al. | |
| 5,998,547 A | 12/1999 | Hohner | |
| 6,017,859 A | 1/2000 | Rossi et al. | |
| 6,022,929 A | 2/2000 | Chen et al. | |
| 6,043,401 A | 3/2000 | Bagheri et al. | |
| 6,049,017 A | 4/2000 | Vora et al. | |
| 6,087,460 A | 7/2000 | Marks et al. | |
| 6,114,445 A | 9/2000 | Tzoganakis et al. | |
| 6,114,457 A | 9/2000 | Markel et al. | |
| 6,114,477 A | 9/2000 | Merrill et al. | |
| 6,117,962 A * | 9/2000 | Weng et al. | 526/351 |
| 6,133,209 A | 10/2000 | Rath et al. | |
| 6,143,686 A | 11/2000 | Vizzini et al. | |
| 6,143,846 A | 11/2000 | Herrmann et al. | |
| 6,143,942 A | 11/2000 | Verrelst et al. | |
| 6,147,173 A | 11/2000 | Holtcamp | |
| 6,147,180 A | 11/2000 | Markel et al. | |
| 6,184,327 B1 | 2/2001 | Weng et al. | |
| 6,197,910 B1 | 3/2001 | Weng et al. | |
| 6,207,606 B1 | 3/2001 | Lue et al. | |
| 6,211,108 B1 | 4/2001 | Bishop et al. | |
| 6,225,432 B1 | 5/2001 | Weng et al. | |
| 6,248,832 B1 | 6/2001 | Peacock | |
| 6,258,903 B1 | 7/2001 | Mawson et al. | |
| 6,262,202 B1 | 7/2001 | Walzer, Jr. et al. | |
| 6,268,518 B1 | 7/2001 | Resconi et al. | |
| 6,271,323 B1 | 8/2001 | Loveday et al. | |
| 6,291,695 B1 | 9/2001 | Marks et al. | |
| 6,297,301 B1 | 10/2001 | Erderly et al. | |
| 6,323,284 B1 | 11/2001 | Peacock | |
| 6,342,574 B1 | 1/2002 | Weng et al. | |
| 6,407,189 B1 | 6/2002 | Herrmann | |
| 6,410,666 B1 | 6/2002 | Grubbs et al. | |
| 6,414,090 B2 | 7/2002 | Minami et al. | |
| 6,414,091 B2 | 7/2002 | Moritomi et al. | |
| 6,423,793 B1 | 7/2002 | Weng et al. | |
| 6,444,773 B1 | 9/2002 | Markel | |
| 6,448,350 B1 | 9/2002 | Dall'Occo et al. | |
| 6,476,167 B2 | 11/2002 | Peters | |
| 6,548,724 B2 | 4/2003 | Bagheri et al. | |
| 6,555,635 B2 | 4/2003 | Markel | |
| 6,569,965 B2 | 5/2003 | Markel et al. | |
| 6,573,350 B1 | 6/2003 | Markel et al. | |
| 6,576,306 B2 | 6/2003 | Mehta et al. | |
| 6,635,597 B1 | 10/2003 | Marks et al. | |
| 6,646,081 B2 | 11/2003 | Godschalx et al. | |
| 6,660,809 B1 | 12/2003 | Weng et al. | |
| 6,703,457 B2 | 3/2004 | Van Baar et al. | |
| 6,706,828 B2 | 3/2004 | DiMaio | |
| 6,713,438 B1 | 3/2004 | Baillargeon et al. | |
| 6,750,307 B2 | 6/2004 | Weng et al. | |
| 6,774,191 B2 | 8/2004 | Weng et al. | |
| 6,780,936 B1 | 8/2004 | Agarwal et al. | |
| 6,809,168 B2 | 10/2004 | Agarwal et al. | |
| 6,884,914 B2 | 4/2005 | Mathys et al. | |
| 6,897,261 B1 | 5/2005 | Machida et al. | |
| 6,927,265 B2 | 8/2005 | Kaspar et al. | |
| 6,939,930 B2 | 9/2005 | Reinking et al. | |
| 6,977,287 B2 | 12/2005 | Agarwal et al. | |
| 7,005,491 B2 | 2/2006 | Weng et al. | |
| 7,101,936 B2 | 9/2006 | Weng et al. | |
| 7,126,031 B2 | 10/2006 | Boussie et al. | |
| 7,183,359 B2 | 2/2007 | Hanna et al. | |
| 7,223,822 B2 | 5/2007 | Abhari et al. | |
| 7,247,385 B1 | 7/2007 | Tzoganakis et al. | |
| 7,256,240 B1 | 8/2007 | Jiang et al. | |
| 7,276,567 B2 | 10/2007 | Voskoboynikov et al. | |
| 7,294,681 B2 | 11/2007 | Jiang et al. | |
| 7,297,653 B2 | 11/2007 | Rodriguez | |
| 7,297,806 B2 | 11/2007 | Brookhart, III et al. | |
| 7,339,018 B2 | 3/2008 | Arjunan | |
| RE40,751 E * | 6/2009 | Jejelowo et al. | 526/160 |
| 7,541,402 B2 | 6/2009 | Abhari et al. | |
| 7,550,528 B2 | 6/2009 | Abhari et al. | |
| 7,589,160 B2 | 9/2009 | Resconi et al. | |
| 7,700,707 B2 | 4/2010 | Abhari et al. | |
| 7,820,607 B2 | 10/2010 | Matsuda et al. | |
| 7,943,716 B2 | 5/2011 | Resconi et al. | |
| 7,960,487 B2 | 6/2011 | Yang et al. | |
| 8,022,142 B2 | 9/2011 | Jiang et al. | |
| 8,058,351 B2 | 11/2011 | Pawlow et al. | |
| 8,207,390 B2 * | 6/2012 | Wu et al. | 585/523 |
| 2001/0007896 A1 | 7/2001 | Agarwal et al. | |
| 2001/0053837 A1 | 12/2001 | Agarwal et al. | |
| 2002/0013440 A1 | 1/2002 | Agarwal et al. | |
| 2002/0137978 A1 | 9/2002 | Grubbs et al. | |
| 2003/0055184 A1 | 3/2003 | Song et al. | |
| 2003/0161752 A1 | 8/2003 | Luk et al. | |
| 2004/0127614 A1 | 7/2004 | Jiang et al. | |
| 2004/0127649 A1 | 7/2004 | Arjunan et al. | |
| 2004/0127654 A1 | 7/2004 | Brant et al. | |
| 2004/0138392 A1 | 7/2004 | Jiang et al. | |
| 2004/0214953 A1 | 10/2004 | Yamada et al. | |
| 2004/0220320 A1 | 11/2004 | Abhari et al. | |
| 2004/0220336 A1 | 11/2004 | Abhari et al. | |
| 2004/0249046 A1 | 12/2004 | Abhari et al. | |
| 2005/0054793 A1 | 3/2005 | Reinking et al. | |
| 2005/0159299 A1 | 7/2005 | Rodriguez et al. | |
| 2005/0261440 A1 | 11/2005 | Dickakian et al. | |
| 2006/0052553 A1 | 3/2006 | Resconi et al. | |
| 2006/0199873 A1 | 9/2006 | Mehta et al. | |
| 2006/0270814 A1 | 11/2006 | Makio et al. | |
| 2006/0293453 A1 | 12/2006 | Jiang et al. | |
| 2006/0293455 A1 | 12/2006 | Jiang et al. | |
| 2006/0293460 A1 | 12/2006 | Jacob et al. | |
| 2006/0293461 A1 | 12/2006 | Jiang et al. | |
| 2006/0293462 A1 | 12/2006 | Jacob et al. | |
| 2007/0129497 A1 | 6/2007 | Jiang et al. | |
| 2007/0265178 A1 | 11/2007 | Patil et al. | |
| 2007/0282073 A1 | 12/2007 | Weng et al. | |
| 2007/0284787 A1 | 12/2007 | Weng et al. | |
| 2007/0293640 A1 | 12/2007 | Jiang et al. | |
| 2008/0177121 A1 | 7/2008 | Wu et al. | |
| 2008/0228017 A1 | 9/2008 | Burdett et al. | |
| 2008/0234451 A1 | 9/2008 | Kenwright et al. | |
| 2009/0105423 A1 | 4/2009 | Pawlow et al. | |
| 2009/0221750 A1 | 9/2009 | Tsunogae et al. | |
| 2009/0247441 A1 | 10/2009 | Baum | |
| 2009/0318640 A1 | 12/2009 | Brant et al. | |
| 2009/0318644 A1 | 12/2009 | Brant et al. | |
| 2009/0318646 A1 | 12/2009 | Brant et al. | |

(56) References Cited

U.S. PATENT DOCUMENTS

| | | |
|---|---|---|
| 2009/0318647 A1 | 12/2009 | Hagadorn et al. |
| 2010/0069573 A1 | 3/2010 | Arriola et al. |
| 2010/0152387 A1 | 6/2010 | Steininger et al. |
| 2010/0152388 A1 | 6/2010 | Jiang et al. |

FOREIGN PATENT DOCUMENTS

| | | |
|---|---|---|
| GB | 1 310 847 | 3/1973 |
| JP | 02-064115 | 3/1990 |
| JP | 1993/320260 | 3/1993 |
| JP | 2000/038418 | 2/2000 |
| JP | 2000/038420 | 2/2000 |
| JP | 2000/080134 | 3/2000 |
| JP | 2005/009158 | 1/2005 |
| JP | 2005/139284 | 6/2005 |
| JP | 2005/336092 | 12/2005 |
| JP | 2006/002057 | 1/2006 |
| JP | 2007/169340 | 7/2007 |
| JP | 2007/246433 | 9/2007 |
| JP | 2008/050278 | 3/2008 |
| JP | 2009/299045 | 12/2009 |
| JP | 2010/037555 | 2/2010 |
| JP | 2011/026448 | 2/2011 |
| JP | 2012/051859 | 3/2012 |
| JP | 2012/052062 | 3/2012 |
| WO | WO 93/12151 | 6/1993 |
| WO | WO 93/21242 | 10/1993 |
| WO | WO 95/27717 | 10/1995 |
| WO | WO 96/23751 | 8/1996 |
| WO | WO 97/09296 | 3/1997 |
| WO | WO 97/47665 | 12/1997 |
| WO | WO 98/32784 | 7/1998 |
| WO | WO 98/49229 | 11/1998 |
| WO | WO 99/05182 | 2/1999 |
| WO | WO 99/07788 | 2/1999 |
| WO | WO 99/46270 | 9/1999 |
| WO | WO 00/00576 | 1/2000 |
| WO | WO 00/37514 | 6/2000 |
| WO | WO 00/55218 | 9/2000 |
| WO | WO 01/09200 | 2/2001 |
| WO | WO 01/42322 | 6/2001 |
| WO | WO 01/81493 | 11/2001 |
| WO | WO 02/34795 | 5/2002 |
| WO | WO 02/50145 | 6/2002 |
| WO | WO 02/079127 | 10/2002 |
| WO | WO 2004/026923 | 4/2004 |
| WO | WO 2004/031250 | 4/2004 |
| WO | WO 2005/092935 | 10/2005 |
| WO | WO 2006/127483 | 11/2006 |
| WO | WO 2007/003238 | 1/2007 |
| WO | WO 2007/011459 | 1/2007 |
| WO | WO 2007/018743 | 2/2007 |
| WO | WO 2008/027268 | 3/2008 |
| WO | WO 2008/141941 | 11/2008 |
| WO | WO 2009/009158 | 1/2009 |
| WO | WO 2009/155517 | 12/2009 |

OTHER PUBLICATIONS

Britovsek et al., *Iron and Cobalt Ethylene Polymerization Catalysts Bearing 2,6- Bis(Imino)Pyridyl Ligands: Synthesis, Structures, and Polymerization Studies*, Journal of the American Chemical Society, 1999, vol. 121, No. 38, pp. 8728-8740.

Brzezinska et al., *Synthesis of ABA Triblock Copolymers via Acyclic Diene Metathesis Polymerization and Living Polymerization of α-Amino Acid-N-Carboxyanhydrides*, Macromolecules, 2001, vol. 34, pp. 4348-4354.

Bujadoux et al., *Use of bridged and non-bridged metallocene catalysts in high pressure/high temperature ethylene/α-olefin copolymerization*, Metallocene Polymers, 1995, pp. 377-402.

Corey et al., "*Reactions of Hydrosilanes and Olefins in the Presence of $Cp_2MCl_2/nBuLi$*", Organometallics, 1992, vol. 11, pp. 672-683.

Hansell et al., *Additive-Free Clicking for Polymer Functionalization and Coupling by Tetrazine-Norbornene Chemistry*, Journal of the American Chemical Society, 2011, vol. 133, No. 35, pp. 13828-13831.

Herzon et al., "*Direct, Catalytic Hydroaminoalkylation of Unactivated Olefins with N-Alkyl Arylamines*", JACS, 2007, vol. 129, pp. 6690-6691.

Herzon et al., "*Hydroaminoalkylation of Unactivated Olefins with Dialkylamines*", JACS, 2007, vol. 130, pp. 14940-14941.

Kesti et al., "*Group 4 Metallocene Olefin Hydrosilyation Catalysts*", Organometallics, 1992, vol. 11, pp. 1095-1103.

Koo et al., "*Silicon-Modified Ziegler-Natta Polymerization. Catalytic Approaches to Silyl-Capped and Silyl-Linked Polyolefins Using "Single-Site" Cationic Ziegler-Natta Catalysts*", Journal of American Chemical Society, 1999, vol. 121, pp. 8791-8802.

Liu et al., *Kinetics of Initiation, Propagation, and Termination for the [rac-(C2H4(1-indenyl)2)ZrMe]{MeB(C6F5)3}-Catalyzed Polymerization of 1-Hexene*, Journal of the American Chemical Society, 2001, vol. 123, pp. 11193-11207.

Nagai et al., *Novel Well-defined Funcationalized Polyolefins and Polyolefin-polar Polymer Block Copolymers: Formations and Their Features*, Poly Preprints, 2008, vol. 49, No. 2, 776-777.

Nakatsuka et al., *Creation and Application of New Materials by a Fusion of FI-catalyst Technology and Fine Organic Synthesis Technology*, Shokubai, 2010, vol. 52, No. 8, pp. 569-574.

Passaglia et al., "*Grafting of Diethyl Maleate and Maleic Anhydride Onto Styrene-b-(Ethyleneco-1-Butene)-b-Styrene Triblock Copolymer (SEBS)*", Polymer, 2000, vol. 41, pp. 4389-4400.

Quirk et al., "*Anionic Synthesis of Secondary Amine Functionalized Polymers by Reaction of Polymeric Organolithiums with N-Benzylidenemethylamine*" Macromolecular Chemistry and Physics, 2002, vol. 203, pp. 1178-1187.

Rodriguez et al., *Poly(4-vinylpyridazine). First Synthesis, Characterization and Properties*, Polymeric Materials Science and Engineering, Proceedings of the ACS Division of Polymeric Materials Science and Engineering, 1990, vol. 63, pp. 376-382 (Abstract).

Rybak et al., "*Acyclic Diene Metathesis with a Monomer with a Monomer from Renewable Resources: Control of Molecular Weight and One-Step Preparation of Block Copolymers*", ChemSusChem, 2008, vol. 1, pp. 542-547.

Weng et al., Long Chain Branched Isotactic Polypropylene, Macromolecules, 2002, vol. 35, pp. 3838-3843.

Wu et al., *Synthesis of Polynorbornen-poly(ethylene-co-propylene) Diblock Copolymers*, Polymeric Materials Science and Engineering, 1998, vol. 78, pp. 158-159.

Xu et al., *Ethylene Copolymerization with 1-Octene Using a 2-Methylbenz[e]indenyl-Based ansa-Monocyclopentadienylamido Complex and Methylaluminoxane Catalyst*, Macromolecules, 1998, vol. 31, pp. 4724-4729.

Advincula et al., *Polymer Brushes: Synthesis, Characterization, Applications*, Materials Characterization, 2005, vol. 55, pp. 249.

Alonzo et al., *Structure and Scaling Behavior of Polymer Brushes with Multiple Tethers*, Polymer Preprints, 2007, vol. 48, No. 1, pp. 781-782.

Amin et al., *Versatile Pathways for In Situ Polyolefin Functionalization with Heteroatoms: Catalytic Chain Transfer*, Angew. Chem. Int. Ed., 2008, vol. 47, No. 11, pp. 2006-2025.

Brintzinger et al., Stereospecific Olefin Polymerization with Chiral Metallocene Catalysts, Angew. Chem. Int. Ed. Engl., 1995, 34, pp. 1143-1170.

Britovsek et al., *Novel Olefin Polymerization Catalysts Based on Iron and Cobalt*, Chemical Communications, 1998, No. 7, pp. 849-850.

Busico et al., [1] *H NMR Analysis of Chain Unsaturations in Ethene/1-Octene Copolymers Prepared with Metallocene Catalysts at High Temperature*, Macromolecules, 2005, vol. 38, No. 16, pp. 6988-6996.

Chen et al., *Entropically Driven Phase Separation of Highly Branched/Linear Polyolefin Blends*, Journal of Polymer Science, Part B: Polymer Physics, 2000, vol. 38, No. 22, pp. 2965-2975.

Chen et al., Reactive & Functional Polymers, 2008, vol. 68, No. 9, pp. 1307-1313.

(56) References Cited

OTHER PUBLICATIONS

Cheng et al., *Facile One-Pot Synthesis of Brush Polymers through Tandem Catalysis Using Grubbs' Catalyst for Both Ring-Opening Metathesis and Atom Transfer Radical Polymerizations*, Nano Letters, 2006, vol. 6, No. 8, pp. 1741-1746.

Chung, *Synthesis of Functional Polyolefin Copolymers with Graft and Block Structures*, Progress in Polymer Science, 2002, vol. 27, No. 1, pp. 39-85.

Ciolino et al., *Novel Synthesis of Polyethylene-Poly(dimethylsiloxane) Copolymers with a Metallocene Catalyst*, Journal of Polymer Science, Part A: Polymer Chemistry, 2004, vol. 42, No. 10, pp. 2462-2473.

Synthesis of Allyl-Terminated Syndiotactic of Branched Polyolefins, Macromonomers for the Synthesis of Branched Polyolefins, Macromol., 2005, 38, pp. 6259-6268.

Coates, Precise Control of Polyolefin Stereochemistry Using Single-Site Metal Catalysts, Chem. Rev., 2000, 100, pp. 1223-1252.

Cossy et al., "*Cross-Metathesis reaction. Generation of Highly Functionalized Olefins from Unsaturated Alcohols*", Journal of Organometallic Chemistry, 2001, vol. 634, Issue 2, pp. 216-221.

Cosyns, et al., "*Process for Upgrading $C_3$, $C_4$ and $C_5$ Olefinic Streams*", Pet. & Coal, 1995, vol. 37, No. 4, pp. 23-33.

Deeken et al., *How Common Are True Aminopyridinato Complexes?*, Z. Anorg. Allg. Chem., 2007, vol. 633, pp. 320-325.

Dekmezian et al., *Characterization and Modeling of Metallocene-Based Branch-Block Copolymers*, Macromolecules, 2002, vol. 35, No. 25, pp. 9586-9594.

Ding et al., *The Preparation of 3, 6-Bis(3-hexylthien-2-yl)-s-tetrazine and Its Conjugated Polymers*, Journal of Polymer Science Part A: Polymer Chemistry, 2011, vol. 49, No. 15, pp. 3374-3386.

Doi et al., "*Living*" Coordination Polymerization of Propene with a Highly Active Vanadium-Based Catalyst, Macromolecules, 1986, vol. 19, No. 12, pp. 2896-2900.

Doring et al, European Journal of Inorganic Chemistry, 2010, No. 18, pp. 2853-2860.

Djalali et al., *Amphipolar Core-shell Cylindrical Brushes*, Macromolecular Rapid Communications, 1999, vol. 20, No. 8, pp. 444-449.

Elvers et al., Ullmann's Encyclopedia of Industrial Chemistry, vol. A13, VCH Verlagsgesellschaft mbH, Weinheim, 1989, pp. 243-247 and 275-276.

Eshuis, et al., "*Catalytic Olefin Oligomerization and polymerization with cationic group IV metal complexes $[Cp*2Mme(THT)]^+[BH_4]^-$, M=Ti, Zr and Hf*", Journal of Molecular Catalysis, 1990, vol. 62, pp. 277-287.

Ewen et al., Syndiospecific Propylene Polymerizations with Group 4 Metallocenes, J. Am. Chem. Soc., 1988, 110, pp. 6255-6256.

Flory, *Molecular Size Distribution in Ethylene Oxide Polymers*, Journal of American Chemical Society, 1940, vol. 62, No. 6, pp. 1561-1565.

Glatz et al., *First Row Transition Metal Aminopyridinates—the Missing Complexes*, Eur. J. Inorg. Chem., 2009, No. 10, pp. 1385-1392.

Hajela et al., Competitive Chain Transfer by β-Hydrogen and β-methyl Elimination for the Model Ziegler-Natta Olefin Polymerization System $[Me_2Si(\eta^5-C_5Me_4)2]Sc\{CH_2CH(CH_3)_2\}(PMe_3)$, Organometallics, 1994, 13, pp. 1147-1154.

Jagtap et al., *Atomic Force Microscopy (AFM): Basics and Its Important Applications for Polymer Characterization: An Overview*, Journal of Polymer Material, 2005, vol. 21, No. 1, pp. 1-26.

Janiak et al., "*Metallocene Catalysts for Olefin Oligomerization*", Macromol. Symp., 2006, vol. 236, pp. 14-22.

Johnson et al., *Copolymerization of Ethylene and Propylene with Functionalized Vinyl Monomers by Palladium (II) Catalysts*, Journal of American Chemical Society, 1996, vol. 118, No. 1, pp. 267-268.

Kaneyoshi, Hiromu et al., Synthesis of Block and Graft Copolymers with Linear Polyethylene Segments by Combination of Degenerative Transfer Coordination Polymerization and Atom Transfer Radical Polymerization, Macromolecules, 38, 2005, pp. 5425-5435.

Kaneyoshi et al., *Synthesis of a Linear Polyethylene Macromonomer and Preparation of Polystyrenegraft-Polyethylene Copolymers via Grafting-Through Atom Transfer Radical Polymerization*, Journal of Applied Polymer Science, 2007, vol. 105, No. 1, pp. 3-13.

Kawahara et al., *The Detailed Analysis of the Vinylidene Structure of Metallocene-catalyzed Polypropylene*, Polymer, 2004, vol. 45, No. 2, pp. 355-357.

Kim et al., *The Synthesis of Random Brush for Nanostructure of Block Copolymer*, Macromol. Symp., 2007, vol. 249-250, pp. 303-306.

Klep et al., *Nanoparticles: Synthesis, Passivation, Stabilization and Functionalization*, The 233rd ACS National Meeting, Chicago, IL, Mar. 25-29, 2007, Coll 124, Abstract.

Kolodka et al., "*Copolymerization of Propylene with Poly(Ethylene-Co-Propylene) Macromonomer and Branch Chain-Length Dependence of Rheological Properties*", Macromolecules, 2002, vol. 35, pp. 10062-10070.

Labinger et al., Metal-Hydride and Metal-Alkyl Bond Strengths: The Influence of Electronegativity Differences, Organometallics, 1988, 7 pp. 926-928.

Lahitte et al., *Homopolymerization of ω-Allyl or ω-Undecenyl Polystyrene Macromonomers via Coordination Polymerization*, Polymer Preprint, ACS, Div. Of Polym. Chem., 2003, vol. 44, No. 2, pp. 46-47.

Lahitte et al., *Homopolymerization of ωStyryl-Polystyrene Macromonomers in the Presence of CpTiF 3/MAO*, Macromolecular Rapid Communications, 2004, vol. 25, No. 10, pp. 1010-1014.

Lahitte et al., *Design of New Styrene Enriched Polyethylenes via Coordination Copolymerization of Ethylene with Mono- or α, ωdifunctional Polystyrene Macromonomers*, Polymer, 2006, vol. 47, No. 4, pp. 1063-1072.

Nikopoulou et al., "*Anionic Homo- and Copolymerization of Styrenic Triple-Tailed Polybutadiene Macromonomers*", Journal of Polymer Science: Part A-Polymer Chemistry, 2007, vol. 45, Issue 16, pp. 3513-3523.

Kapnistos et al., "*Linear Rheology of Comb Polymers with Star-Like Backbones: Melts and Solutions*", Rheologica Acta, 2006, vol. 46, No. 2, pp. 273-286.

Lopez et al., *Synthesis of Well-defined Polymer Architectures by Successive Catalytic Olefin Polymerization and Living/Controlled Polymerization Reactions*, Progress in Polymer Science, 2007, vol. 32, No. 4, pp. 419-454.

McNamee et al., *Preparation and Characterization of Pure and Mixed Monolayers of Poly(ethylene Glycol) Brushes Chemically Adsorbed to Silica Surfaces*, Langmuir, 2007, vol. 23, No. 8, pp. 4389-4399.

Markel, et al., "*Metallocene-Based Branch-Block Thermoplastic Elastomers*", Macromolecules, 2000, vol. 33, pp. 8541-8548.

Mathers et al., *Cross Metathesis Functionalization of Polyolefins*, Chemical Communications—Chemcom, Royal Society of Chemistry, 2004, No. 4, pp. 422-423.

*Functional Star, Comb, Brush and (Hyper)Branched Polymers by a ATRP*, Polymeric Materials: Science & Engineering, 2001, vol. 84, pp. 363-364.

Mazzolini et al., *Polyethylene End Functionalization Using Radical-Mediated Thiol-Ene Chemistry: Use of Polyethylenes Containing Alkene End Functionality*, Macromolecules, 2011, vol. 44, pp. 3381-3387.

Moscardi et al., "*Propene Polymerization with the Isospecfic, Highly Regioselective rac-$Me_2C(3$-$t$-$Bu$-$l$-$Ind)_2ZrCl_2/MAO$ Catalyst. 2. Combined DFT/MM Analysis of Chain Propagation and Chain Release Reactions*", Organometallics 2001, vol. 20, pp. 1918-1931.

Ornelas et al., *Efficient Mono- and Bifunctionalization of Poly-olefin Dendrimers by Olefin Metathesis*, Angew. Chem. Int. Ed., 2005, vol. 44, No. 45, pp. 7399-7404.

Ornelas et al., *Cross Olefin Metathesis for the Selective Functionalization, Ferrocenylation, and Solubilization in Water of Olefin-Terminated Dendrimers, Polymers, and Gold Nanoparticles and for a Divergent Dendrimer Constructions*, Journal of American Chemical Society, 2008, vol. 130, No. 4, pp. 1495-1506.

Patil et al., *New Monomers and Comb Polymers*, The 233rd ACS National Meeting, Chicago, IL, Mar. 25-29, 2007, BMGT 17, Abstract.

(56) References Cited

OTHER PUBLICATIONS

Rathgeber, et al., "Bottle-brush Macromolecules in Solution: Comparison Between Results Obtained from Scattering Experiments and Computer Simulations", Polymer, 2006, vol. 47, pp. 7318-7327.

Rathgebar et al., On the Shape of Bottle-Brush Macromolecules: Systematic Variation of Architectural Parameters, The Journal of Chemical Physics, 2005, vol. 122, No. 12, pp. 124904-1 and 124904-13.

Resconi et al., Chain Transfer Reactions in Propylene Polymerization with Zirconocene Catalysts, Topics in Catalysis, 1999, vol. 7, No. 1-4, pp. 145-163.

Resconi et al., Selectivity in Propene Polymerization with Metallocene Catalysts, Chem. Rev., 2000, 100, pp. 1253-1345.

Resconi, et al., "Olefin Polymerization at Bis(pentamethylcyclopentadienyl)zirconium and—hafnium Centers: Chain-Transfer Mechanisms," J. Am. Chem. Soc., 1992, vol. 114, pp. 1025-1032.

Rose et al., "Poly(ethylene-co-propylene macromonomer)s: Synthesis and Evidence for Starlike Conformaitons in Dilute Solution", Macromolecules, 2008, vol. 41, pp. 559-567.

Rulhoff, et al., "Synthesis and Characterization of Defined Branched Poly(propylene)s with Different Microstructures by Copolymerization of Propylene and Linear Ethylene Oligomers ($C_n$=26-28) with Metallocenes", Macromolecular Chemistry and Physics, 2006, vol. 207, pp. 1450-1460.

Sainath et al., Synthesis and Characteristics of Succinic Anhydride- and Disodium Succinate-Terminated Low Molecular Weight Polyethylenes, Macromolecules, Communication to the Editor, 2009, pp. A-C, 2009.

Sainath et al., Synthesis and Characteristics of Succinic Anhydride- and Disodium Succinate-Termintaed Low Molecular Weight Polyethylenes, Mitsui Chemicals, Inc., Research Center, Japan, pp. S1-S12.

Schulz, Über die Beziehung zwischen Reaktionsgeschwindigkeit and Zusammensetzung des Reaktionsproduktes bei Makropolymerisationsvorgängen, Phys. Chem. Abst. B, 1935, 30, pp. 379-398.

Schulze et al., Synthesis of Poly(propene-g-styrene) Graft Copolymers by Metallocene Catalyzed Copolymerization of Propene with Allyl-Terminated Polystyrene Macromonomer Obtained via Quasiliving Atom Transfer Radical Polymerization and the Effect of the Grafts on Blending Polypropene with Polystyrene, Macromolecules, 2003, vol. 36, No. 13, pp. 4719-4726.

Scott et al., Di- and Trivalent Lanthanide Complexes Stabilized by Sterically Demanding Aminopyridianto Ligands, Eur. J. Inorg. Chem., 2005, pp. 1319-1324.

Seppäläet al., Polymerization and Characterization of Long-Chain Branched Polyethylene Obtained via Metallocene Catalysts, Polymer Preprint, ACS, Div. Polym. Chem., 2003, vol. 44, No. 2, pp. 26.

Shiono et al., Copolymerization of poly(propylene) macromonomer with ethylene by (tert-butanamide)dimethyl(tetramethyl-qscyclopentadienyl) silane titanium dichloride/methylaluminoxane catalyst, Macromol. Chem. Phys., 1997, vol. 198, pp. 3229-3237.

Shiono et al., Copolymerization of Atactic Polypropene Macromonomer with Propene by an Isospecific Metallocene Catalyst, Macromolecules, 1999, 32, pp. 5723-5727.

Small, et al., "Polymerization of Propylene by a New Generation of Iron Catalysts: Mechanisms of Chain Initiation, Propagation, and Termination", Macromolecules, 1999, vol. 32, pp. 2120-2130.

Small et al., Highly Active Iron and Cobalt Catalysts for the Polymerization of Ethylene, Journal of American Chemical Society, 1998, vol. 120, No. 16, pp. 4049-4050.

Sokoloff, Theory of Friction Between Neutral Polymer Brushes, Macromolecules, 2007, vol. 40, No. 11, pp. 4053-4058.

Sun et al., Iron Complexes Bearing 2-Imino-1,10-phenanthrolinyl Ligands as Highly Active Catalysts for Ethylene Oligomerization, Organometallics, 2006, vol. 25, No. 3, pp. 666-677.

Sun et al., Effect of Short Chain Branching on the Coil Dimensions of Polyolefins in Dilute Solution, Macromolecules, 2001, vol. 34, No. 19, pp. 6812-6820.

Tellmann et al., Selective Dimerization/Oligomerization of α-Olefins by Cobalt Bis(imino)pyridine Catalysts Stabilized by Trifluoromethyl Substituents: Group 9 Metal Catalysts with Productivities Matching Those of Iron Systems, Organometallics, 2005, vol. 24, No. 2, pp. 280-286.

Toyota et al., Synthesis of terminally functionalized polyolefins, Polymer Bulletin 48, 2002, pp. 213-219.

VanderHart et al., Effect of Tacticity on the Structure of Poly(1-octadecene), Macromolecular Chemistry and Physics, 2004, vol. 205, No. 14, pp. 1877-1885.

Vogt, Oligomerization of Ethylene to Higher Linear α-Olefins, B. Cornils et al., Editors, Applied Homogeneous Catalysis with Organometallic Compounds, A Comprehensive Handbook, vol. 1, VCH Verlagsgesellschaft mbH, Weinheim, 1996, pp. 245-258.

Wasilke et al., "Concurrent Tandem Catalysis", Chemical Rev, 2005, vol. 105, pp. 1001-1020.

Weng et al., Synthesis of Long-Chain Branched Propylene Polymers via Macromonomer Incorporation, Macromol. Rapid Commun., 2001, vol. 22, No. 18, pp. 1488-1492.

Weng et al., Synthesis of Vinyl-Terminated Isotactic Poly(propylene), Macromol. Rapid Commun., 2000, 21, No. 16, pp. 1103-1107.

Wintermantel et al., Molecular Bottlebrushes, Macromolecules, 1996, vol. 29, No. 3, pp. 978-983.

Yang, et al., "Cationic Metallocene Polymerization Catalysts, Synthesis and Properties of the First Base-Free Zirconocene Hydride", Angew. Chem. Intl. Edn. Engl., 1992, vol. 31, pp. 1375-1377.

Zhang et al., Conformation of Cylindrical Brushes in Solution: Effect of Side Chain Length, Macromolecules, 2006, vol. 39, No. 24, pp. 8440-8450.

Zhao et al., Comb-Coil Polymer Brushes on the Surface of Silica Nanoparticles, Macromolecules, 2005, vol. 38, No. 26, pp. 10619-10622.

Zhu et al., Synthesis and Characterization of Long-Chain-Branched Polyolefins with Metallocene Catalysts: Copolymerization of Ethylene with Poly(ethylene-co-propylene) Macromonomer, Macromol. Rap. Commun., 2003, 24, pp. 311-315.

* cited by examiner

HIGH VINYL TERMINATED PROPYLENE BASED OLIGOMERS

CROSS-REFERENCE TO RELATED APPLICATIONS

This application is a divisional of U.S. Pat. No. 8,372,930, issued Feb. 12, 2013.

FIELD OF THE INVENTION

This invention relates to olefin oligomerization, particularly propylene-ethylene oligomerization, to produce vinyl terminated oligomers.

BACKGROUND OF THE INVENTION

Alpha-olefins, especially those containing about 6 to about 20 carbon atoms, have been used as intermediates in the manufacture of detergents or other types of commercial products. Such alpha-olefins have also been used as monomers, especially in linear low density polyethylene. Commercially produced alpha-olefins are typically made by oligomerizing ethylene. Longer chain alpha-olefins, such as vinyl-terminated polyethylenes are also known and can be useful as building blocks following functionalization or as macromonomers.

Allyl terminated low molecular weight solids and liquids of ethylene or propylene have also been produced, typically for use as branches in polymerization reactions. See, for example, Rulhoff, Sascha and Kaminsky, ("*Synthesis and Characterization of Defined Branched Poly(propylene)s with Different Microstructures by Copolymerization of Propylene and Linear Ethylene Oligomers ($C_n$=26-28) with Metallocenes/MAO Catalysts*," Macromolecules 16 2006, 1450-1460), and Kaneyoshi, Hiromu et al. ("*Synthesis of Block and Graft Copolymers with Linear Polyethylene Segments by Combination of Degenerative Transfer Coordination Polymerization and Atom Transfer Radical Polymerization*," Macromolecules 38 2005, 5425-5435).

Further, U.S. Pat. No. 4,814,540 discloses bis(pentamethyl cyclopentadienyl)hafnium dichloride, bis(pentamethyl cyclopentadienyl) zirconium dichloride and bis(tetramethyl n-butyl cyclopentadienyl)hafnium dichloride with methylalumoxane in toluene or hexane with or without hydrogen to make allylic vinyl terminated propylene homo-oligomers having a low degree of polymerization of 2-10. These oligomers do not have high Mn's and have at least 93% allylic vinyl unsaturation. Likewise, these oligomers lack comonomer and are produced at low productivities with a large excess of alumoxane (molar ratio≥600 Al/M; M=Zr, Hf). Additionally, no less than 60 wt % solvent (solvent+propylene basis) is present in all of the examples.

Teuben et al. (J. Mol. Catal. 62 1990, 277-87) used [Cp*$_2$MMe(THT)]+[BPh$_4$], M=Zr and Hf) to make propylene oligomers. For M=Zr a broad product distribution with oligomers up to $C_{24}$ (Mn 336) was obtained at room temperature. Whereas for M=Hf only the dimer 4-methyl-1-pentene and the trimer 4,6-dimethyl-1-heptene were formed. The dominant termination mechanism appeared to be beta-methyl transfer from the growing chain back to the metal center, as was demonstrated by deuterium labeling studies.

X. Yang, et al. (Angew. Chem. Intl Edn. Engl. 31 1992 1375) discloses amorphous, low molecular weight polypropylene made at low temperatures where the reactions showed low activity and product having 90% allylic vinyls, relative to all unsaturations, by $^1$H NMR. Thereafter, Resconi, et al. (J. Am. Chem. Soc. 114 1992, 1025-1032), disclose the use of bis(pentamethylcyclopentadienyl) zirconium and bis(pentamethylcyclopentadienyl)hafnium centers to polymerize propylene and obtained beta-methyl termination resulting in oligomers and low molecular weight polymers with "mainly allyl- and iso-butyl-terminated" chains. As is the case in U.S. Pat. No. 4,814,540, the oligomers produced do not have at least 93% allyl chain ends, an Mn of about 500 to about 20,000 g/mol (as measured by $^1$H NMR), and the catalyst has low productivity (1-12,620 g/mmol metallocene.hr;>3000 wppm Al in products).

Similarly, Small and Brookhart, (*Macromol.* 32 1999, 2322) discloses the use of a pyridylbis amido iron catalyst in a low temperature polymerization to produce low molecular weight amorphous propylene materials apparently having predominant or exclusive 2,1 chain growth, chain termination via beta-hydride elimination, and high amounts of vinyl end groups. Dekmezian et al. (*Macromol.* 33, 2000, 8541-8548) discloses materials with up to about 81 percent vinyl termination made using dimethylsilyl bis(2-methyl, 4-phenyl-indenyl) hafnium dichloride and methylalumoxane in toluene at about 120° C. The materials have a number average molecular weight of about 12,300 (measured with $^1$H NMR) and a melting point of about 143° C.

Moscardi et al. (*Organomet.* 20, 2001, 1918) discloses the use of rac-dimethylsilylmethylene bis(3-t-butyl indenyl) zirconium dichloride with methylalumoxane in batch polymerizations of propylene to produce materials where " . . . allyl end group always prevails over any other end groups, at any [propene]." In these reactions, morphology control was limited and approximately 60% of the chain ends are allylic.

Coates et al. (*Macromol* 2005 38, 6259) discloses preparation of low molecular weight syndiotactic polypropylene ([rrrr]=0.46-0.93) with about 100% allyl end groups using bis(phenoxyimine)titanium dichloride ((PHI)$_2$TiCl$_2$) activated with modified methyl alumoxane (MMAO; Al/Ti molar ratio=200) in batch polymerizations run between −20 and +20° C. for four hours. For these polymerizations, propylene was dissolved in toluene to create a 1.65 M toluene solution. Catalyst productivity was very low (0.95 to 1.14 g/mmol Ti/hr).

JP-2005-336092-A2 discloses the manufacture of vinyl-terminated propylene polymers using materials such as H$_2$SO$_4$ treated montmorillonite, triethylaluminum, triisopropyl aluminum, where the liquid propylene is fed into a catalyst slurry in toluene. This process produces substantially isotactic macromonomers not having a significant amount of amorphous material.

Rose et al (Macromolecules 2008, 41, 559-567) discloses poly(ethylene-co-propylene) macromonomers not having significant amounts of iso-butyl chain ends. Those were made with bis(phenoxyimine) titanium dichloride ((PHI)$_2$TiCl$_2$) activated with modified methylalumoxane (MMAO; Al/Ti molar ratio range 150 to 292) in semi-batch polymerizations (30 psi propylene added to toluene at 0° C. for 30 min, followed by ethylene gas flow at 32 psi of over-pressure at about 0° C. for polymerization times of 2.3 to 4 hours to produce E-P copolymer having an Mn of about 4800 to 23,300. In four reported copolymerizations, allylic chain ends decreased with increasing ethylene incorporation roughly according to the equation:

$$\% \text{ allylic chain ends (of total unsaturations)} = -0.95 \text{ (mole \% ethylene incorporated)} + 100.$$

For example, 65% allyl (compared to total unsaturation) was reported for E-P copolymer containing 29 mole % ethylene. This is the highest allyl population achieved. For 64 mole % incorporated ethylene, only 42% of the unsaturations are allylic. Productivity of these polymerizations ranged from $0.78 \times 10^2$ g/mmol Ti/hr to $4.62 \times 10^2$ g/mmol Ti/hr.

Prior to this work, Zhu et al. reported only low (~38%) vinyl terminated ethylene-propylene copolymer made with the constrained geometry metallocene catalyst $[C_5Me_4(SiMe_2N\text{-tert-butyl})TiMe_2$ activated with $B(C_6F_5)_3$ and MMAO (*Macromol* 2002 35, 10062-10070 and *Macromol Rap. Commun.* 2003 24 311-315).

Janiak and Blank summarize a variety of work related to oligomerization of olefins (Macromol. Symp. 236 2006, 14-22).

In all the prior art no catalysts are shown to produce high allylic chain unsaturations in high yields, a wide range of molecular weight, and with high productivity for propylene-based polymerizations, especially propylene-ethylene copolymerizations. Thus, there is still a need for propylene based macromonomers that have allyl termination present in high amounts (90% or more), with control over a wide range of molecular weights that can be made at commercial temperatures (e.g. 25° C. and above) and commercial rates (5,000 g/mmol/hr productivity or more). Alternately, there is a need for propylene ethylene oligomers having structural robustness (where addition of ethylene raises viscosity and the solubility parameter—relative to propylene—and provides for potential crystallizable ethylene runs, while lowering glass transition temperature). Further, there is a need for propylene based reactive materials having vinyl termination which can be functionalized and used in additive applications.

SUMMARY OF THE INVENTION

This invention relates to a propylene co-oligomer having an Mn of 300 to 30,000 g/mol (as measured by $^1$H NMR) comprising 10 to 90 mol % propylene and 10 to 90 mol % of ethylene, wherein the oligomer has at least X % allyl chain ends (relative to total unsaturations), where: 1) X=(−0.94*(mole % ethylene incorporated)+100), when 10 to 60 mole % ethylene is present in the co-oligomer, and 2) X=45, when greater than 60 and less than 70 mole % ethylene is present in the co-oligomer, and 3) X=(1.83*(mole % ethylene incorporated)−83), when 70 to 90 mole % ethylene is present in the co-oligomer.

This invention further relates to a propylene oligomer, comprising more than 90 mol % propylene and less than 10 mol % ethylene, wherein the oligomer has: at least 93% allyl chain ends, an Mn of about 500 to about 20,000 g/mol (as measured by $^1$H NMR), an isobutyl chain end to allylic vinyl group ratio of 0.8:1 to 1.35:1.0, and less than 1400 ppm aluminum.

This invention further relates to a propylene oligomer, comprising at least 50 mol % propylene and from 10 to 50 mol % ethylene, wherein the oligomer has: at least 90% allyl chain ends, Mn of about 150 to about 10,000 g/mol (as measured by $^1$H NMR), and an isobutyl chain end to allylic vinyl group ratio of 0.8:1 to 1.3:1.0, wherein monomers having four or more carbon atoms are present at from 0 to 3 mol %.

This invention further relates to a propylene oligomer, comprising at least 50 mol % propylene, from 0.1 to 45 mol % ethylene, and from 0.1 to 5 mol % C4 to C12 olefin, wherein the oligomer has: at least 87% allyl chain ends (alternately at least 90%), an Mn of about 150 to about 10,000 g/mol, (as measured by $^1$H NMR), and an isobutyl chain end to allylic vinyl group ratio of 0.8:1 to 1.35:1.0.

This invention further relates to a propylene oligomer, comprising at least 50 mol % propylene, from 0.1 to 45 mol % ethylene, and from 0.1 to 5 mol % diene, wherein the oligomer has: at least 90% allyl chain ends, an Mn of about 150 to about 10,000 g/mol (as measured by $^1$H NMR), and an isobutyl chain end to allylic vinyl group ratio of 0.7:1 to 1.35:1.0.

This invention further relates to a homooligomer, comprising propylene, wherein the oligomer has: at least 93% allyl chain ends, an Mn of about 500 to about 20,000 g/mol (as measured by $^1$H NMR), an isobutyl chain end to allylic vinyl group ratio of 0.8:1 to 1.2:1.0, and less than 1400 ppm aluminum.

This invention further relates to a homogeneous process to make such oligomers.

DETAILED DESCRIPTION

Figure 1:
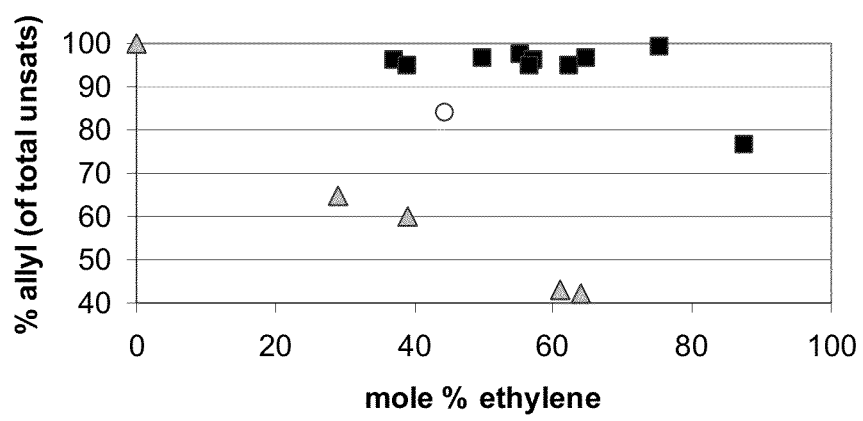
FIG. 1 is a plot of percent allylic chain ends versus mole % ethylene for Examples 35 and 52 to 61. (The triangles are data from Macromolecules 2008, 41, 559-567. The squares represent Examples 52 to 61 and the circle represents Example 35.)

This invention relates to a propylene homo oligomer, comprising propylene and less than 0.5 wt % comonomer, preferably 0 wt % comonomer, wherein the oligomer has:
  i) at least 93% allyl chain ends (preferably at least 95%, preferably at least 97%, preferably at least 98%);
  ii) a number average molecular weight (Mn) of about 500 to about 20,000 g/mol, as measured by $^1$H NMR (preferably 500 to 15,000, preferably 700 to 10,000, preferably 800 to 8,000 g/mol, preferably 900 to 7,000, preferably 1000 to 6,000, preferably 1000 to 5,000);
  iii) an isobutyl chain end to allylic vinyl group ratio of 0.8:1 to 1.3:1.0;
  iv) less than 1400 ppm aluminum, (preferably less than 1200 ppm, preferably less than 1000 ppm, preferably less than 500 ppm, preferably less than 100 ppm).

This invention relates to a propylene co-oligomer having an Mn of 300 to 30,000 g/mol as measured by $^1$H NMR (preferably 400 to 20,000, preferably 500 to 15,000, preferably 600 to 12,000, preferably 800 to 10,000, preferably 900 to 8,000, preferably 900 to 7,000 g/mol), comprising 10 to 90 mol % propylene (preferably 15 to 85 mol %, preferably 20 to 80 mol %, preferably 30 to 75 mol %, preferably 50 to 90 mol %) and 10 to 90 mol % (preferably 85 to 15 mol %, preferably 20 to 80 mol %, preferably 25 to 70 mol %, preferably 10 to 50 mol %) of one or more alpha-olefin comonomers (preferably ethylene, butene, hexene, or octene, preferably ethylene), wherein the oligomer has at least X % allyl chain ends (relative to total unsaturations), where: 1) X=(−0.94(mole % ethylene incorporated)+100 {alternately 1.20 (−0.94(mole % ethylene incorporated)+100), alternately 1.50(−0.94(mole % ethylene incorporated)+100)}), when 10 to 60 mole % ethylene is present in the co-oligomer, and 2) X=45 (alternately 50, alternately 60), when greater than 60 and less than 70 mole % ethylene is present in the co-oligomer, and 3) X=(1.83*(mole % ethylene incorporated)−83, {alternately 1.20 [1.83*(mole % ethylene incorporated)−83], alternately 1.50 [1.83*(mole % ethylene incorporated)−83]}), when 70 to 90 mole % ethylene is present in the co-oligomer.

Alternately X is 80% or more, preferably 85% or more, preferably 90% or more, preferably 95% or more.

In an alternate embodiment the oligomer has at least 80% isobutyl chain ends (based upon the sum of isobutyl and n-propyl saturated chain ends), preferably at least 85% isobutyl chain ends, preferably at least 90% isobutyl chain ends. Alternately, the oligomer has an isobutyl chain end to allylic vinyl group ratio of 0.8:1 to 1.35:1.0, preferably 0.9:1 to 1.20:1.0, preferably 0.9:1.0 to 1.1:1.0.

This invention relates to a propylene oligomer, comprising more than 90 mol % propylene (preferably 95 to 99 mol %, preferably 98 to 9 mol %) and less than 10 mol % ethylene (preferably 1 to 4 mol %, preferably 1 to 2 mol %), wherein the oligomer has:

at least 93% allyl chain ends (preferably at least 95%, preferably at least 97%, preferably at least 98%);

a number average molecular weight (Mn) of about 400 to about 30,000 g/mol, as measured by $^1$H NMR (preferably 500 to 20,000, preferably 600 to 15,000, preferably 700 to 10,000 g/mol, preferably 800 to 9,000, preferably 900 to 8,000, preferably 1000 to 6,000);

an isobutyl chain end to allylic vinyl group ratio of 0.8:1 to 1.35:1.0, and less than 1400 ppm aluminum, (preferably less than 1200 ppm, preferably less than 1000 ppm, preferably less than 500 ppm, preferably less than 100 ppm).

This invention also relates to a propylene oligomer, comprising:

at least 50 (preferably 60 to 90, preferably 70 to 90) mol % propylene and from 10 to 50 (preferably 10 to 40, preferably 10 to 30) mol % ethylene, wherein the oligomer has:

at least 90% allyl chain ends (preferably at least 91%, preferably at least 93%, preferably at least 95%, preferably at least 98%);

an Mn of about 150 to about 20,000 g/mol, as measured by $^1$H NMR (preferably 200 to 15,000, preferably 250 to 15,000, preferably 300 to 10,000, preferably 400 to 9,500, preferably 500 to 9,000, preferably 750 to 9,000); and an isobutyl chain end to allylic vinyl group ratio of 0.8:1 to 1.3:1.0, wherein monomers having four or more carbon atoms are present at from 0 to 3 mol % (preferably at less than 1 mol %, preferably less than 0.5 mol %, preferably at 0 mol %).

This invention further relates to a propylene oligomer, comprising:

at least 50 (preferably at least 60, preferably 70 to 99.5, preferably 80 to 99, preferably 90 to 98.5) mol % propylene, from 0.1 to 45 (preferably at least 35, preferably 0.5 to 30, preferably 1 to 20, preferably 1.5 to 10) mol % ethylene, and from 0.1 to 5 (preferably 0.5 to 3, preferably 0.5 to 1) mol % $C_4$ to $C_{12}$ olefin (such as butene, hexene or octene, preferably butene), wherein the oligomer has:

at least 90% allyl chain ends (preferably at least 91%, preferably at least 93%, preferably at least 95%, preferably at least 98%);

a number average molecular weight (Mn) of about 150 to about 15,000 g/mol, as measured by $^1$H NMR (preferably 200 to 12,000, preferably 250 to 10,000, preferably 300 to 10,000, preferably 400 to 9500, preferably 500 to 9,000, preferably 750 to 9,000); and an isobutyl chain end to allylic vinyl group ratio of 0.8:1 to 1.35:1.0.

This invention further relates to a propylene oligomer, comprising:

at least 50 (preferably at least 60, preferably 70 to 99.5, preferably 80 to 99, preferably 90 to 98.5) mol % propylene, from 0.1 to 45 (preferably at least 35, preferably 0.5 to 30, preferably 1 to 20, preferably 1.5 to 10) mol % ethylene, and from 0.1 to 5 (preferably 0.5 to 3, preferably 0.5 to 1) mol % diene (such as C4 to C12 alpha-omega dienes (such as butadiene, hexadiene, octadiene), norbornene, ethylidene norbornene, vinylnorbornene, norbornadiene, and dicyclopentadiene), wherein the oligomer has:

at least 90% allyl chain ends (preferably at least 91%, preferably at least 93%, preferably at least 95%, preferably at least 98%);

a number average molecular weight (Mn) of about 150 to about 20,000 g/mol, as measured by $^1$H NMR (preferably 200 to 15,000, preferably 250 to 12,000, preferably 300 to 10,000, preferably 400 to 9,500, preferably 500 to 9,000, preferably 750 to 9,000); and an isobutyl chain end to allylic vinyl group ratio of 0.7:1 to 1.35:1.0.

Any of the oligomers prepared herein preferably have less than 1400 ppm aluminum, preferably less than 1000 ppm aluminum, preferably less than 500 ppm aluminum, preferably less than 100 ppm aluminum, preferably less than 50 ppm aluminum, preferably less than 20 ppm aluminum, preferably less than 5 ppm aluminum.

This invention also relates to a homogeneous process, preferably a bulk process, to make such oligomers.

As used herein, the term "oligomer" is defined to have an Mn of from 100 to 25,000 g/mol as measured by $^1$H NMR. When an oligomer is referred to as comprising an olefin, the olefin present in the oligomer is the oligomerized form of the olefin. A propylene oligomer is an oligomer having at least 50 mole % of propylene. A co-oligomer is an oligomer comprising at least two different monomer units (such as propylene and ethylene). A homo-oligomer is an oligomer comprising units of the same monomer (such as propylene). As used herein, Mn is number average molecular weight (measured by $^1$H NMR unless stated otherwise, as for example in Table 3A), Mw is weight average molecular weight (measured by Gel Permeation Chromatography), and Mz is z average molecular weight (measured by Gel Permeation Chromatography), wt % is weight percent, and mol % is mole percent. Molecular weight distribution (MWD) is defined to be Mw (measured by Gel Permeation Chromatography) divided by Mn (measured by $^1$H NMR). Unless otherwise noted, all molecular weight units (e.g., Mw, Mn, Mz) are g/mol.

"Allyl chain ends" is defined to be an oligomer having at least one terminus represented by ($CH_2CH$—$CH_2$-oligomer), formula I:

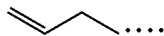

allylic vinyl end group where the "••••" represents the oligomer chain. In a preferred embodiment the allyl chain ends is represented by the formula II:

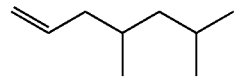

allylic vinyl end group

The amount of allyl chain ends is determined using $^1$H NMR at 120° C. using deuterated tetrachloroethane as the solvent on a 500 MHz machine. and in selected cases confirmed by $^{13}$C NMR. Resconi has reported proton and carbon assignments (neat perdeuterated tetrachloroethane used for proton spectra while a 50:50 mixture of normal and perdeuterated tetrachloroethane was used for carbon spectra; all spectra were recorded at 100° C. on a Bruker AM 300 spectrometer operating at 300 MHz for proton and 75.43 MHz for carbon) for vinyl terminated propylene oligomers in J American Chemical Soc 114 1992, 1025-1032 that are useful herein.

"Isobutyl chain end" is defined to be an oligomer having at least one terminus represented by the formula:

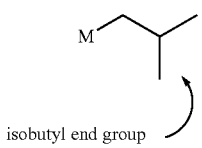

isobutyl end group where M represents the oligomer chain. In a preferred embodiment, the isobutyl chain end is represented by one of the following formulae:

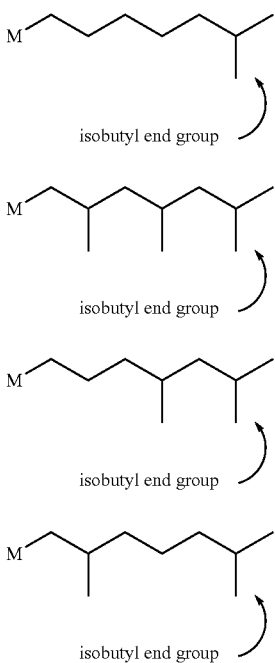

where M represents the oligomer chain.

Figure 2:
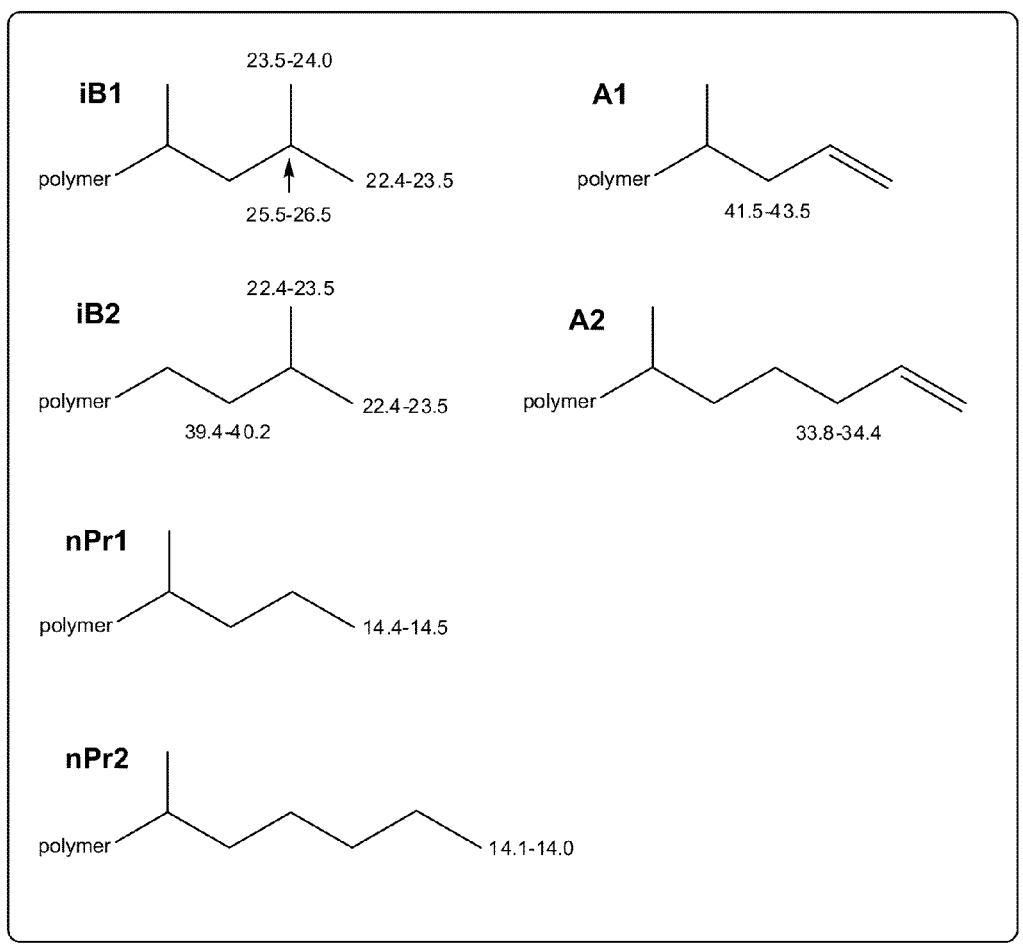
FIG. 2 is a chart of the range of chemical shift assignments for the isobutyl chain ends for the E-P copolymers.

The percentage of isobutyl end groups is determined using $^{13}C$ NMR (as described in the example section) and the chemical shift assignments in Resconi et al, J. Am. Chem. Soc. 1992, 114, 1025-1032 for 100% propylene oligomers and set forth in FIG. 2 for E-P oligomers.

The "isobutyl chain end to allylic vinyl group ratio" is defined to be the ratio of the percentage of isobutyl chain ends to the percentage of allylic vinyl groups.

In a preferred embodiment, the propylene oligomer comprises less than 3 wt % of functional groups selected from hydroxide, aryls and substituted aryls, halogens, alkoxys, carboxylates, esters, acrylates, oxygen, nitrogen, and carboxyl, preferably less than 2 wt %, more preferably less than 1 wt %, more preferably less than 0.5 wt %, more preferably less than 0.1 wt %, more preferably 0 wt %, based upon the weight of the oligomer.

The oligomer preferably has an M. as determined by $^1H$ NMR of 150 to 25,000 g/mole, 200 to 20,000 g/mol, preferably 250 to 15,000 g/mol, preferably 300 to 15,000 g/mol, preferably 400 to 12,000 g/mol, preferably 750 to 10,000 g/mol. Further a desirable molecular weight range can be any combination of any upper molecular weight limit with any lower molecular weight limit described above. $M_n$ is determined according to the methods described below in the examples section.

The oligomer preferably has a glass transition temperature (Tg) of 0° C. or less (as determined by differential scanning calorimetry as described below), preferably –10° C. or less, more preferably –20° C. or less, more preferably –30° C. or less, more preferably –50° C. or less.

The oligomer preferably contains less than 80 weight % of $C_4$ olefin(s), (such as isobutylene n-butene, 2-butene, isobutylene, and butadiene), based upon the weight of the oligomer, preferably less than 10 wt %, preferably 5 wt %, preferably less than 4 wt %, preferably less than 3 wt %, preferably less than 2 wt %, preferably less than 1 wt %, preferably less than 0.5 wt %, preferably less than 0.25 wt % of $C_4$ olefin(s) based upon the weight of the oligomer.

Alternately, the oligomer preferably contains less than 20 weight % of $C_4$ or more olefin(s), (such as $C_4$ to $C_{30}$ olefins, typically such as $C_4$ to $C_{12}$ olefins, typically such as $C_4$, $C_6$, $C_8$, $C_{12}$, olefins, etc.), based upon the weight of the oligomer, preferably less than 10 wt %, preferably 5 wt %, preferably less than 4 wt %, preferably less than 3 wt %, preferably less than 2 wt %, preferably less than 1 wt %, preferably less than 0.5 wt %, preferably less than 0.25 wt % of $C_4$ olefin(s) based upon the weight of the oligomer, as determined by $^{13}C$ NMR.

In another embodiment, the oligomer composition produced comprises at least 50 wt % (preferably at least 75 wt %, preferably at least 90 wt %, based upon the weight of the oligomer composition) olefins having at least 36 carbon atoms (preferably at least 51 carbon atoms, preferably at least 102 carbon atoms) as measured by $^1H$ NMR assuming one unsaturation per chain.

In another embodiment, the oligomer composition produced comprises less than 20 wt % dimer and trimer (preferably less than 10 wt %, preferably less than 5 wt %, more preferably less than 2 wt %, based upon the weight of the oligomer composition), as measured by GC.

In another embodiment, the oligomer produced here contains less than 25 ppm hafnium, preferably less than 10 ppm hafnium, preferably less than 5 ppm hafnium based on the yield of polymer produced and the mass of catalyst employed.

In another embodiment, the oligomers described herein may have a melting point (DSC first melt) of from 60 to 130° C., alternately 50 to 100° C. In another embodiment, the oligomers described herein have no detectable melting point by DSC following storage at ambient temperature (23° C.) for at least 48 hours.

Melting temperature ($T_m$) and glass transition temperature (Tg) are measured using Differential Scanning calorimetry (DSC) using commercially available equipment such as a TA Instruments 2920 DSC. Typically, 6 to 10 mg of the sample, that has been stored at room temperature for at least 48 hours, is sealed in an aluminum pan and loaded into the instrument at room temperature. The sample is equilibrated at 25° C., then it is cooled at a cooling rate of 10° C./min to –80° C. The sample is held at –80° C. for 5 min and then heated at a heating rate of 10° C./min to 25° C. The glass transition temperature is measured from the heating cycle. Alternatively, the sample is equilibrated at 25° C., then heated at a heating rate of 10° C./min to 150° C. The endothermic melting transition, if present, is analyzed for onset of transition and peak temperature. The melting temperatures reported are the peak melting temperatures from the first heat unless otherwise specified. For samples displaying multiple peaks, the melting point (or melting temperature) is defined to be the peak melting temperature (i.e., associated with the largest endothermic calorimetric response in that range of temperatures) from the DSC melting trace.

In another embodiment, the oligomers described herein are a liquid at 25° C.

In another embodiment, the oligomers described herein have an Mw (measured as described below) of 1,000 to about 30,000 g/mol, alternately 2000 to 25,000 g/mol, alternately 3,000 to 20,000 g/mol and/or an Mz of about 1700 to about 150,000 g/mol, alternately 800 to 100,000 g/mol.

Mw and Mz are measured by using a High Temperature Size Exclusion Chromatograph (either from Waters Corporation or Polymer Laboratories), equipped with a differential refractive index detector (DRI), Experimental details, are described in: T. Sun, P. Brant, R. R. Chance, and W. W. Graessley, Macromolecules, Volume 34, Number 19, 6812-6820, (2001) and references therein. Three Polymer Laboratories PLgel 10 mm Mixed-B columns are used. The nominal flow rate is 0.5 cm$^3$/min, and the nominal injection volume is 300 μl. The various transfer lines, columns and differential refractometer (the DRI detector) are contained in an oven maintained at 135° C. Solvent for the SEC experiment is prepared by dissolving 6 grams of butylated hydroxy toluene as an antioxidant in 4 liters of Aldrich reagent grade 1, 2, 4 trichlorobenzene (TCB). The TCB mixture is then filtered through a 0.7 μm glass pre-filter and subsequently through a 0.1 μm Teflon filter. The TCB is then degassed with an online degasser before entering the SEC. Polymer solutions are prepared by placing dry polymer in a glass container, adding the desired amount of TCB, then heating the mixture at 160° C. with continuous agitation for about 2 hours. All quantities are measured gravimetrically. The TCB densities used to express the polymer concentration in mass/volume units are 1.463 g/ml at room temperature and 1.324 g/ml at 135° C. The injection concentration is from 1.0 to 2.0 mg/ml, with lower concentrations being used for higher molecular weight samples. Prior to running each sample the DRI detector and the injector are purged. Flow rate in the apparatus is then increased to 0.5 ml/minute, and the DRI is allowed to stabilize for 8 to 9 hours before injecting the first sample. The concentration, c, at each point in the chromatogram is calculated from the baseline-subtracted DRI signal, $I_{DRI}$, using the following equation:

$$c = K_{DRI} I_{DRI}/(dn/dc)$$

where $K_{DRI}$ is a constant determined by calibrating the DRI, and (dn/dc) is the refractive index increment for the system. The refractive index, n=1.500 for TCB at 135° C. and λ=690 nm. For purposes of this invention and the claims thereto (dn/dc)=0.104 for propylene polymers and 0.1 otherwise. Units on parameters throughout this description of the SEC method are such that concentration is expressed in g/cm$^3$, molecular weight is expressed in g/mole, and intrinsic viscosity is expressed in dL/g.

Molecular weight distribution (Mw/Mn—by GPC-DRI) is determined by the method above. In some embodiments, the oligomers of this invention have an Mw/Mn (by GPC-DRI) of 1.5 to 20, alternately 1.7 to 10.

Oligomerization Process

This invention also relates to a homogeneous process, preferably a bulk process, to make the oligomers described herein. In a preferred embodiment, propylene and optional comonomers (such as ethylene) can be oligomerized by reacting a catalyst system (comprising metallocene compound(s), and one or more activators) with the olefins. Other additives may also be used, as desired, such as scavengers and/or hydrogen. Any conventional suspension, homogeneous bulk, solution, slurry, or high-pressure oligomerization process can be used. Such processes can be run in a batch, semi-batch, or continuous mode. Such processes and modes are well known in the art. Homogeneous polymerization processes are preferred. (A homogeneous polymerization process is defined to be a process where at least 90 wt % of the product is soluble in the reaction media.) A bulk homogeneous process is particularly preferred. (A bulk process is defined to be a process where monomer concentration in all feeds to the reactor is 70 volume % or more.) Alternately no solvent or diluent is present or added in the reaction medium, (except for the small amounts used as the carrier for the catalyst system or other additives, or amounts typically found with the monomer; e.g. propane in propylene).

Suitable diluents/solvents for oligomerization include non-coordinating, inert liquids. Examples include straight and branched-chain hydrocarbons such as isobutane, butane, pentane, isopentane, hexanes, isohexane, heptane, octane, dodecane, and mixtures thereof; cyclic and alicyclic hydrocarbons such as cyclohexane, cycloheptane, methylcyclohexane, methylcycloheptane, and mixtures thereof such as can be found commercially (Isopars); perhalogenated hydrocarbons such as perfluorinated $C_{4-10}$ alkanes, chlorobenzene, and aromatic and alkylsubstituted aromatic compounds such as benzene, toluene, mesitylene, and xylene. Suitable solvents also include liquid olefins which may act as monomers or comonomers including ethylene, propylene, 1-butene, 1-hexene, 1-pentene, 3-methyl-1-pentene, 4-methyl-1-pentene, 1-octene, and 1-decene. Mixtures of the foregoing are also suitable.

In a preferred embodiment, the feed concentration for the oligomerization is 60 volume % solvent or less, preferably 40 volume % or less, preferably 20 volume % or less. Preferably the oligomerization is run in a bulk process.

Suitable additives to the oligomerization process can include one or more scavengers, promoters, modifiers, reducing agents, oxidizing agents, hydrogen, aluminum alkyls, or silanes.

In a preferred embodiment hydrogen is present in the oligomerization reactor at a partial pressure of 0.001 to 50 psig, preferably from 0.01 to 25 psig, more preferably 0.1 to 10 psig. It has been found that in the present systems, hydrogen can be used to provide increased activity without significantly impairing the catalyst's ability to produce allylic chain ends. Preferably the catalyst activity (calculated as g/mmolcatalyst/hr) is at least 20% higher than the same reaction without hydrogen present, preferably at least 50% higher, preferably at least 100% higher.

In an alternate embodiment, the productivity at least 4500 g/mmol/hour, preferably 5000 or more g/mmol/hour, preferably 10,000 or more g/mmol/hr, preferably 50,000 or more g/mmol/hr.

In an alternate embodiment, the productivity is at least 80,000 g/mmol/hr, preferably at least 150,000 g/mmol/hr, preferably at least 200,000 g/mmol/hr, preferably at least 250,000 g/mmol/hr, preferably at least 300,000 g/mmol/hr.

Preferred oligomerizations can be run at typical temperatures and/or pressures, such as from 25 to 150° C., preferably 40 to 120° C., preferably 45 to 80° C., and preferably from 0.35 to 10 MPa, preferably 0.45 to 6 MPa, preferably from 0.5 to 4 MPa.

In a typical oligomerization, the residence time of the reaction is up to 60 minutes, preferably between 5 to 50 minutes, preferably 10 to 40 minutes.

Catalyst Compound

Catalyst compounds useful herein include one or more metallocene compound(s) represented by the formulae:

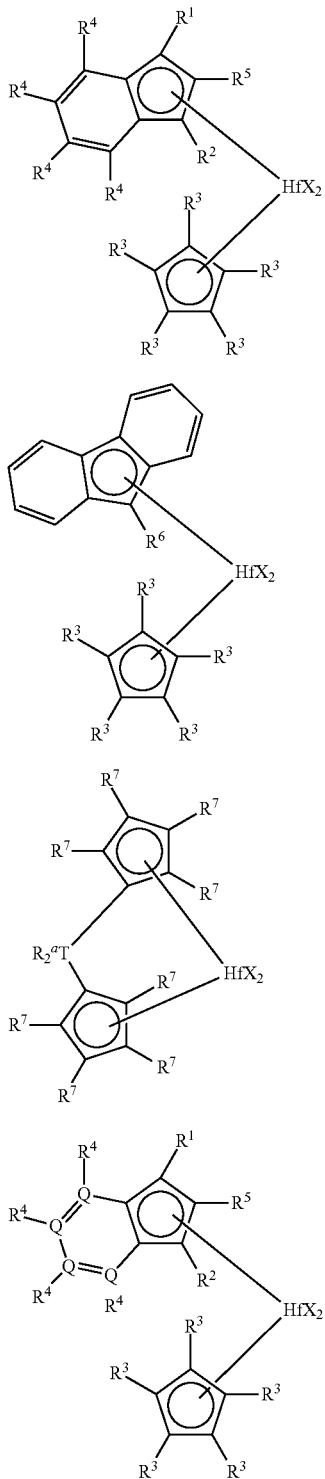

where
Hf is hafnium;
each X is, independently, selected from the group consisting of hydrocarbyl radicals having from 1 to 20 carbon atoms, hydrides, amides, alkoxides, sulfides, phosphides, halogens, dienes, amines, phosphines, ethers, or a combination thereof, preferably methyl, ethyl, propyl, butyl, phenyl, benzyl, chloride, bromide, iodide, (alternately two X's may form a part of a fused ring or a ring system);

each Q is, independently carbon or a heteroatom, preferably C, N, P, S (preferably at least one Q is a heteroatom, alternately at least two Q's are the same or different heteroatoms, alternately at least three Q's are the same or different heteroatoms, alternately at least four Q's are the same or different heteroatoms);

each $R^1$ is, independently, hydrogen or a $C_1$ to $C_8$ alkyl group, preferably a $C_1$ to $C_8$ linear alkyl group, preferably methyl ethyl, propyl, butyl, pentyl, hexyl, heptyl or octyl, $R^1$ may the same or different as $R^2$;

each $R^2$ is, independently, hydrogen or a $C_1$ to $C_8$ alkyl group, preferably a $C_1$ to $C_8$ linear alkyl group, preferably methyl ethyl, propyl, butyl, pentyl, hexyl, heptyl or octyl, provided that at least one of $R^1$ or $R^2$ is not hydrogen, preferably both of $R^1$ and $R^2$ are not hydrogen, preferably $R^1$ and/or $R^2$ are not branched;

each $R^3$ is, independently, hydrogen, or a substituted or unsubstituted hydrocarbyl group having from 1 to 8 carbon atoms, preferably 1 to 6 carbon atoms, preferably a substituted or unsubstituted $C_1$ to $C_8$ linear alkyl group, preferably methyl ethyl, propyl, butyl, pentyl, hexyl, heptyl, octyl, provided however that at least three $R^3$ groups are not hydrogen (alternately four $R^3$ groups are not hydrogen, alternately five $R^3$ groups are not hydrogen); {Alternately, when the catalyst compound is to used to make the homo-oligomer then each $R^3$ is, independently, hydrogen, or a substituted or unsubstituted hydrocarbyl group having from 1 to 8 carbon atoms, preferably 1 to 6 carbon atoms, preferably a substituted or unsubstituted $C_1$ to $C_8$ linear alkyl group, preferably methyl ethyl, propyl, butyl, pentyl, hexyl, heptyl, octyl, provided however that: 1) all five $R^3$ groups are methyl, or 2) four $R^3$ groups are not hydrogen and at least one $R^3$ group is a $C_2$ to $C_8$ substituted or unsubstituted hydrocarbyl (preferably at least two, three, four or five $R^3$ groups are a $C_2$ to $C_8$ substituted or unsubstituted hydrocarbyl)};

each $R^4$ is, independently, hydrogen or a substituted or unsubstituted hydrocarbyl group, a heteroatom or heteroatom containing group, preferably a substituted or unsubstituted hydrocarbyl group having from 1 to 20 carbon atoms, preferably 1 to 8 carbon atoms, preferably a substituted or unsubstituted $C_1$ to $C_8$ linear alkyl group, preferably methyl ethyl, propyl, butyl, pentyl, hexyl, heptyl, octyl, substituted phenyl (such as propyl phenyl), phenyl, silyl, substituted silyl, (such as $CH_2SiR'$, where R' is a $C_1$ to $C_{12}$ hydrocarbyl, such as methyl, ethyl, propyl, butyl, phenyl);

$R^5$ is hydrogen or a $C_1$ to $C_8$ alkyl group, preferably a $C_1$ to $C_8$ linear alkyl group, preferably methyl, ethyl, propyl, butyl, pentyl, hexyl, heptyl or octyl;

$R^6$ is hydrogen or a $C_1$ to $C_8$ alkyl group, preferably a $C_1$ to $C_8$ linear alkyl group, preferably methyl, ethyl, propyl, butyl, pentyl, hexyl, heptyl or octyl;

each $R^7$ is, independently, hydrogen, or a $C_1$ to $C_8$ alkyl group, preferably a $C_1$ to $C_8$ linear alkyl group, preferably methyl ethyl, propyl, butyl, pentyl, hexyl, heptyl or octyl, provided however that at least seven $R^7$ groups are not hydrogen, alternately at least eight $R^7$ groups are not hydrogen, alternately all $R^7$ groups are not hydrogen, (preferably the $R^7$ groups at the 3 and 4 positions on each Cp ring of Formula IV are not hydrogen);

N is nitrogen;

T is a bridge, preferably, Si or Ge, preferably Si;

each $R^a$, is independently, hydrogen, halogen or a C1 to C20 hydrocarbyl, such as methyl, ethyl, propyl, butyl, pentyl, hexyl, heptyl, octyl, phenyl, benzyl, substituted phenyl, and two $R^a$ can form a cyclic structure including aromatic, partially saturated, or saturated cyclic or fused ring system; and further provided that any two adjacent R groups may form a fused ring or multicenter fused ring system where the rings may be aromatic, partially saturated or saturated.

The term "substituted" means that a hydrogen group has been replaced with a hydrocarbyl group, a heteroatom or a heteroatom containing group. For example methyl cyclopentadiene (Cp) is a Cp group substituted with a methyl group and ethyl alcohol is an ethyl group substituted with an —OH group.

In an alternate embodiment, at least one $R^4$ group is not hydrogen, alternately at least two $R^4$ groups are not hydrogen, alternately at least three $R^4$ groups are not hydrogen, alternately at least four $R^4$ groups are not hydrogen, alternately all $R^4$ groups are not hydrogen.

Catalyst compounds that are particularly useful in this invention include one or more of:

(1,3-Dimethylindenyl)(pentamethylcyclopentadienyl) Hafniumdimethyl,
(1,3,4,7-Tetramethylindenyl)(pentamethylcyclopentadienyl) Hafniumdimethyl,
(1,3-Dimethylindenyl)(tetramethylcyclopentadienyl)Hafniumdimethyl,
(1,3-Diethylindenyl)(pentamethylcyclopentadienyl)Hafniumdimethyl,
(1,3-Dipropylindenyl)(pentamethylcyclopentadienyl)Hafniumdimethyl,
(1-Methyl,3-propyllindenyl)(pentamethylcyclopentadienyl) Hafniumdimethyl,
(1,3-Dimethylindenyl)(tetramethylpropylcyclopentadienyl) Hafniumdimethyl,
(1,2,3-Trimethylindenyl)(pentamethylcyclopentadienyl) Hafniumdimethyl,
(1,3-Dimethylbenzindenyl)(pentamethylcyclopentadienyl) Hafniumdimethyl,
(2,7-Bis t-butylfluorenyl)(pentamethylcyclopentadienyl) Hafniumdimethyl,
(9-Methylfluorenyl)(pentamethylcyclopentadienyl)Hafniumdimethyl,
(2,7,9-Trimethylfluorenyl)(pentamethylcyclopentadienyl) Hafniumdimethyl,
μ-Dihydrosilyl(bis tetramethylcyclopentadienyl)Hafniumdimethyl,
μ-Dihydrosilyl(bis tetramethylcyclopentadienyl)Hafniumdimethyl,
μ-Dimethylsilyl(tetramethylcyclopentadienyl)(3-propyltrimethylcyclopentadienyl)Hafniumdimethyl, and
μ-Dicyclopropylsilyl(bis tetramethylcyclopentadienyl) Hafniumdimethyl.

In an alternate embodiment, the "dimethyl" after the transition metal in the list of catalyst compounds above is replaced with a dihalide (such as dichloride or difluoride) or a bisphenoxide, particularly for use with an alumoxane activator.

Activators and Activation Methods for Catalyst Compounds

The terms "cocatalyst" and "activator" are used herein interchangeably and are defined to be any compound which can activate any one of the catalyst compounds described above by converting the neutral catalyst compound to a catalytically active catalyst compound cation. Non-limiting activators, for example, include alumoxanes, aluminum alkyls, ionizing activators, which may be neutral or ionic, and conventional-type cocatalysts. Preferred activators typically include alumoxane compounds, modified alumoxane compounds, and ionizing anion precursor compounds that abstract one reactive, σ-bound, metal ligand making the metal complex cationic and providing a charge-balancing noncoordinating or weakly coordinating anion.

In one embodiment, alumoxane activators are utilized as an activator in the catalyst composition. Alumoxanes are generally oligomeric compounds containing —Al($R^1$)—O— subunits, where $R^1$ is an alkyl group. Examples of alumoxanes include methylalumoxane (MAO), modified methylalumoxane (MMAO), ethylalumoxane and isobutylalumoxane. Alkylalumoxanes and modified alkylalumoxanes are suitable as catalyst activators, particularly when the abstractable ligand is an alkyl, halide, alkoxide or amide. Mixtures of different alumoxanes and modified alumoxanes may also be used. It may be preferable to use a visually clear methylalumoxane. A cloudy or gelled alumoxane can be filtered to produce a clear solution or clear alumoxane can be decanted from the cloudy solution. Another alumoxane is a modified methyl alumoxane (MMAO) cocatalyst type 3A (commercially available from Akzo Chemicals, Inc. under the trade name Modified Methylalumoxane type 3A, covered under patent number U.S. Pat. No. 5,041,584).

When the activator is an alumoxane (modified or unmodified), some embodiments select the maximum amount of activator at a 5000-fold molar excess Al/M over the catalyst precursor (per metal catalytic site). The minimum activator-to-catalyst-precursor is a 1:1 molar ratio. Alternate preferred ranges include up to 500:1, alternately up to 200:1, alternately up to 100:1 alternately from 1:1 to 50:1.

Aluminum alkyl or organoaluminum compounds which may be utilized as co-activators (or scavengers) include trimethylaluminum, triethylaluminum, triisobutylaluminum, tri-n-hexylaluminum, tri-n-octylaluminum and the like.

Ionizing Activators

It is within the scope of this invention to use an ionizing or stoichiometric activator, neutral or ionic, such as tri (n-butyl) ammonium tetrakis(pentafluorophenyl) borate, a tris perfluorophenyl boron metalloid precursor or a tris perfluoronapthyl boron metalloid precursor, polyhalogenated heteroborane anions (WO 98/43983), boric acid (U.S. Pat. No. 5,942,459) or combination thereof. It is also within the scope of this invention to use neutral or ionic activators alone or in combination with alumoxane or modified alumoxane activators. Much preferred activators are the ionic ones, not the neutral boranes.

Examples of neutral stoichiometric activators include tri-substituted boron, tellurium, aluminum, gallium and indium or mixtures thereof. The three substituent groups are each independently selected from alkyls, alkenyls, halogens, substituted alkyls, aryls, arylhalides, alkoxy and halides. Preferably, the three groups are independently selected from halogen, mono or multicyclic (including halosubstituted) aryls, alkyls, and alkenyl compounds and mixtures thereof, preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). More preferably, the three groups are alkyls having 1 to 4 carbon groups, phenyl, napthyl or mixtures thereof. Even more preferably, the three groups are halogenated, preferably fluorinated, aryl groups. Most preferably, the neutral stoichiometric activator is tris perfluorophenyl boron or tris perfluoronapthyl boron.

Ionic stoichiometric activator compounds may contain an active proton, or some other cation associated with, but not coordinated to, or only loosely coordinated to, the remaining ion of the ionizing compound. Such compounds and the like are described in European publications EP-A-0 570 982, EP-A-0 520 732, EP-A-0 495 375, EP-B1-0 500 944, EP-A-0 277 003 and EP-A-0 277 004, and U.S. Pat. Nos. 5,153,157, 5,198,401, 5,066,741, 5,206,197, 5,241,025, 5,384,299 and 5,502,124 and U.S. patent application Ser. No. 08/285,380, filed Aug. 3, 1994, all of which are herein fully incorporated by reference.

Ionic catalysts can be preparedly reacting a transition metal compound with some neutral Lewis acids, such as $B(C_6F_6)_3$, which upon reaction with the hydrolyzable ligand (X) of the transition metal compound forms an anion, such as $([B(C_6F_5)_3(X)]^-)$, which stabilizes the cationic transition metal species generated by the reaction. The catalysts can be, and preferably are, prepared with activator components which are ionic compounds or compositions.

Compounds useful as an activator component in the preparation of the ionic catalyst systems used in the process of this invention comprise a cation, which is preferably a Bronsted acid capable of donating a proton, and a compatible non-coordinating anion which anion is relatively large (bulky), capable of stabilizing the active catalyst species (the Group 4 cation) which is formed when the two compounds are combined and said anion will be sufficiently labile to be displaced by olefinic, diolefinic and acetylenically unsaturated substrates or other neutral Lewis bases such as ethers, amines and the like. Two classes of compatible non-coordinating anions have been disclosed in EP-A0 277,003 and EP-A0 277,004 published 1988: 1) anionic coordination complexes comprising a plurality of lipophilic radicals covalently coordinated to and shielding a central charge-bearing metal or metalloid core, and 2) anions comprising a plurality of boron atoms such as carboranes, metallacarboranes and boranes.

In a preferred embodiment, the stoichiometric activators include a cation and an anion component, and may be represented by the following formula:

$$(L\text{-}H)_d^+(A^{d-}) \tag{14}$$

wherein L is an neutral Lewis base; H is hydrogen; $(L\text{-}H)^+$ is a Bronsted acid; $A^{d-}$ is a non-coordinating anion having the charge d-; and d is an integer from 1 to 3.

The cation component, $(L\text{-}H)_d^+$ may include Bronsted acids such as protonated Lewis bases capable of protonating a moiety, such as an alkyl or aryl, from the bulky ligand metallocene containing transition metal catalyst precursor, resulting in a cationic transition metal species.

The activating cation $(L\text{-}H)_d^+$ may be a Bronsted acid, capable of donating a proton to the transition metal catalytic precursor resulting in a transition metal cation, including ammoniums, oxoniums, phosphoniums, silyliums, and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxoniums from ethers such as dimethyl ether diethyl ether, tetrahydrofuran and dioxane, sulfoniums from thioethers, such as diethyl thioethers and tetrahydrothiophene, and mixtures thereof.

The anion component $A^{d-}$ include those having the formula $[M^{k+}Q_n]^{d-}$ wherein k is an integer from 1 to 3; n is an integer from 2 to 6; n-k=d; M is an element selected from Group 13 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than 1 occurrence is Q a halide. Preferably, each Q is a fluorinated hydrocarbyl group having 1 to 20 carbon atoms, more preferably each Q is a fluorinated aryl group, and most preferably each Q is a pentafluoryl aryl group. Examples of suitable $A^{d-}$ also include diboron compounds as disclosed in U.S. Pat. No. 5,447,895, which is fully incorporated herein by reference.

Illustrative, but not limiting examples of boron compounds which may be used as an activating cocatalyst in the preparation of the improved catalysts of this invention are tri-substituted ammonium salts such as:

trimethylammonium tetraphenylborate, triethylammonium tetraphenylborate, tripropylammonium tetraphenylborate, tri(n-butyl)ammonium tetraphenylborate, tri(t-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, tropillium tetraphenylborate, triphenylcarbenium tetraphenylborate, triphenylphosphonium tetraphenylborate triethylsilylium tetraphenylborate, benzene(diazonium) tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium)tetrakis (pentafluorophenyl)borate, tropillium tetrakis (pentafluorophenyl)borate, triphenylcarbenium tetrakis (pentafluorophenyl)borate, triphenylphosphonium tetrakis (pentafluorophenyl)borate, triethylsilylium tetrakis (pentafluorophenyl)borate, benzene(diazonium)tetrakis (pentafluorophenyl)borate, trimethylammonium tetrakis-(2,3,4,6-tetrafluorophenyl) borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluoro-phenyl)borate, dimethyl(t-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium)tetrakis-(2,3,4,6-tetrafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium)tetrakis-(2,3,4,6-tetrafluorophenyl)borate, trimethylammonium tetrakis(perfluoronapthyl)borate, triethylammonium tetrakis(perfluoronapthyl)borate, tripropylammonium tetrakis(perfluoronapthyl)borate, tri(n-butyl)ammonium tetrakis(perfluoronapthyl)borate, tri(t-butyl)ammonium tetrakis(perfluoronapthyl)borate, N,N-dimethylanilinium tetrakis(perfluoronapthyl)borate, N,N-diethylanilinium tetrakis(perfluoronapthyl)borate, N,N-dimethyl-(2,4,6-trimethylanilinium)tetrakis(perfluoronapthyl)borate, tropillium tetrakis(perfluoronapthyl)borate, triphenylcarbenium tetrakis(perfluoronapthyl)borate, triphenylphosphonium tetrakis(perfluoronapthyl)borate, triethylsilylium tetrakis(perfluoronapthyl)borate, benzene(diazonium)tetrakis(perfluoronapthyl)borate, trimethylammonium tetrakis(perfluorobiphenyl)borate, triethylammonium tetrakis(perfluorobiphenyl)borate, tripropylammonium tetrakis(perfluorobiphenyl)borate, tri (n-butyl)ammonium tetrakis(perfluorobiphenyl)borate, tri (t-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium)tetrakis (perfluorobiphenyl)borate, tropillium tetrakis (perfluorobiphenyl)borate, triphenylcarbenium tetrakis (perfluorobiphenyl)borate, triphenylphosphonium tetrakis (perfluorobiphenyl)borate, triethylsilylium tetrakis (perfluorobiphenyl)borate, benzene(diazonium)tetrakis (perfluorobiphenyl)borate, trimethylammonium tetrakis (3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis (3,5-bis(trifluoromethyl)phenyl)borate, tri(t-butyl) ammonium tetrakis(3,5-bis(trifluoromethyl)phenyl) borate, N,N-dimethylanilinium tetrakis(3,5-bis (trifluoromethyl)phenyl)borate, N,N-diethylanilinium tetrakis(3,5-bis(trifluoromethyl)phenyl)borate, N,N-dimethyl-(2,4,6-trimethylanilinium)tetrakis(3,5-bis(trifluoromethyl)phenyl)borate, tropillium tetrakis(3,5-bis(trifluoromethyl)phenyl)borate, triphenylcarbenium tetrakis (3,5-bis(trifluoromethyl)phenyl)borate, triphenylphosphonium tetrakis(3,5-bis(trifluoromethyl) phenyl)borate, triethylsilylium tetrakis(3,5-bis(trifluoromethyl)phenyl)borate, benzene(diazonium)tetrakis(3,5-bis(trifluoromethyl)phenyl)borate, and dialkyl ammonium salts such as: di-(i-propyl)ammonium tetrakis(pentafluorophenyl)borate, and dicyclohexylammonium tetrakis (pentafluorophenyl)borate; and additional tri-substituted phosphonium salts such as tri(o-tolyl)phosphonium tetrakis(pentafluorophenyl)borate, and tri(2,6-dimethylphenyl) phosphonium tetrakis(pentafluorophenyl)borate.

Most preferably, the ionic stoichiometric activator $(L-H)_d^+$ $(A^{d-})$ is, N,N-dimethylanilinium tetrakis(perfluoronapthyl)borate, N,N-dimethylanilinium tetrakis(perfluorobiphenyl)borate, N,N-dimethylanilinium tetrakis(3,5-bis (trifluoromethyl)phenyl)borate, triphenylcarbenium tetrakis (perfluoronapthyl)borate, triphenylcarbenium tetrakis (perfluorobiphenyl)borate, triphenylcarbenium tetrakis(3,5-bis(trifluoromethyl)phenyl)borate, or triphenylcarbenium tetrakis(perfluorophenyl)borate.

In one embodiment, an activation method using ionizing ionic compounds not containing an active proton but capable of producing a bulky ligand metallocene catalyst cation and their non-coordinating anion are also contemplated, and are described in EP-A 0 426 637, EP-A 0 573 403 and U.S. Pat. No. 5,387,568, which are all herein incorporated by reference.

The term "non-coordinating anion" (NCA) means an anion which either does not coordinate to said cation or which is only weakly coordinated to said cation thereby remaining sufficiently labile to be displaced by a neutral Lewis base. "Compatible" non-coordinating anions are those which are not degraded to neutrality when the initially formed complex decomposes. Further, the anion will not transfer an anionic substituent or fragment to the cation so as to cause it to form a neutral four coordinate metallocene compound and a neutral by-product from the anion. Non-coordinating anions useful in accordance with this invention are those that are compatible, stabilize the metallocene cation in the sense of balancing its ionic charge at +1, yet retain sufficient lability to permit displacement by an ethylenically or acetylenically unsaturated monomer during polymerization. In addition to these activator compounds or co-catalysts, scavengers are used such as tri-isobutyl aluminum or tri-octyl aluminum.

Invention process also can employ cocatalyst compounds or activator compounds that are initially neutral Lewis acids but form a cationic metal complex and a noncoordinating anion, or a zwitterionic complex upon reaction with the invention compounds. For example, tris(pentafluorophenyl) boron or aluminum act to abstract a hydrocarbyl or hydride ligand to yield an invention cationic metal complex and stabilizing noncoordinating anion, see EP-A 0 427 697 and EP-A 0 520 732 for illustrations of analogous Group-4 metallocene compounds. Also, see the methods and compounds of EP-A 0 495 375. For formation of zwitterionic complexes using analogous Group 4 compounds, see U.S. Pat. Nos. 5,624,878; 5,486,632; and 5,527,929.

Another suitable ion forming, activating cocatalyst comprises a salt of a cationic oxidizing agent and a noncoordinating, compatible anion represented by the formula:

$$(OX^{e+})_d(A^{d-})_e \qquad (16)$$

wherein $OX^{e+}$ is a cationic oxidizing agent having a charge of e+; e is an integer from 1 to 3; and $A^-$, and d are as previously defined. Examples of cationic oxidizing agents include: ferrocenium, hydrocarbyl-substituted ferrocenium, $Ag^+$, or $Pb^{+2}$. Preferred embodiments of $A^{d-}$ are those anions previously defined with respect to the Bronsted acid containing activators, especially tetrakis(pentafluorophenyl)borate.

The typical NCA activator-to-catalyst-precursor ratio is a 1:1 molar ratio. Alternate preferred ranges include from 0.1:1 to 100:1, alternately from 0.5:1 to 200:1, alternately from 1:1 to 500:1 alternately from 1:1 to 1000:1. A particularly useful range is from 0.5:1 to 10:1, preferably 1:1 to 5:1.

Activator Combinations

It is within the scope of this invention that catalyst compounds can be combined with one or more activators or activation methods described above. For example, a combination of activators have been described in U.S. Pat. Nos. 5,153,157 and 5,453,410, European publication EP-B1 0 573 120, and PCT publications WO 94/07928 and WO 95/14044. These documents all discuss the use of an alumoxane in combination with an ionizing activator.

Oligomer Uses

The oligomers prepared herein may be functionalized by reacting a hereroatom containing group with the oligomer with or without a catalyst. Examples include catalytic hydrosilylation, hydroformylation, or hydroamination, or maleation with activators such as free radical generators (e.g. peroxides). The functionalized oligomers can be used in oil additivation and many other applications. Preferred uses include additives for lubricants and or fuels. Preferred heteroatom containing groups include, amines, aldehydes, alcohols, acids, succinic acid, maleic acid and maleic anhydride.

In some embodiments the oligomers produced herein are functionalized as described in U.S. Pat. No. 6,022,929; A. Toyota, T. Tsutsui, and N. Kashiwa, Polymer Bulletin 48, 213-219, 2002; and J. Am. Chem. Soc., 1990, 112, 7433-7434.

In another embodiment this invention relates to:
1. A co-oligomer having an Mn of 300 to 30,000 g/mol comprising 10 to 90 mol % propylene and 10 to 90 mol % of ethylene, wherein the oligomer has at least X % allyl chain ends (relative to total unsaturations as measured by $^1$H NMR), where: 1) X=(−0.94(mole % ethylene incorporated)+100), when 10 to 60 mole % ethylene is present in the co-oligomer, and 2) X=45, when greater than 60 and less than 70 mole % ethylene is present in the co-oligomer, and 3) X=(1.83*(mole % ethylene incorporated)−83), when 70 to 90 mole % ethylene is present in the co-oligomer.

2. The oligomer of paragraph 1 wherein the oligomer has more than 90% allyl chain ends (relative to total unsaturations).
3. The oligomer of paragraph 1 wherein the oligomer comprises at 15 to 95 wt % ethylene and has more than 80% allyl chain ends (relative to total unsaturations).
4. The oligomer of paragraph 1 wherein the oligomer comprises at 30 to 95 wt % ethylene and has more than 70% allyl chain ends (relative to total unsaturations).
5. The oligomer of paragraph 1 wherein the oligomer comprises at 30 to 95 wt % ethylene and has more than 90% allyl chain ends (relative to total unsaturations).
6. A propylene oligomer, comprising more than 90 mol % propylene and less than 10 mol % ethylene wherein the oligomer has: at least 93% allyl chain ends, a number average molecular weight (Mn) of about 500 to about 20,000 g/mol, an isobutyl chain end to allylic vinyl group ratio of 0.8:1 to 1.35:1.0, and less than 1400 ppm aluminum.
7. A propylene oligomer, comprising: at least 50 mol % propylene and from 10 to 50 mol % ethylene, wherein the oligomer has: at least 90% allyl chain ends, an Mn of about 150 to about 10,000 g/mol, and an isobutyl chain end to allylic vinyl group ratio of 0.8:1 to 1.2:1.0, wherein monomers having four or more carbon atoms are present at from 0 to 3 mol %.
8. A propylene oligomer, comprising at least 50 mol % propylene, from 0.1 to 45 mol % ethylene, and from 0.1 to 5 mol % $C_4$ to $C_{12}$ olefin, wherein the oligomer has: at least 90% allyl chain ends, an Mn of about 150 to about 10,000 g/mol, and an isobutyl chain end to allylic vinyl group ratio of 0.8:1 to 1.35:1.0.
9. A propylene oligomer, comprising at least 50 mol % propylene, from 0.1 to 45 mol % ethylene, and from 0.1 to 5 mol % diene, wherein the oligomer has: at least 90% allyl chain ends, an Mn of about 150 to about 10,000 g/mol, and an isobutyl chain end to allylic vinyl group ratio of 0.7:1 to 1.35:1.0.
10. A homo-oligomer, comprising propylene, wherein the oligomer has: at least 93% allyl chain ends, an Mn of about 500 to about 20,000 g/mol, an isobutyl chain end to allylic vinyl group ratio of 0.8:1 to 1.2:1.0, and less than 1400 ppm aluminum.
11. The oligomer of any of paragraphs 1 to 10, wherein the oligomer is a liquid at 25° C.
12. The oligomer of any of paragraphs 1-11, wherein the Mn is about 500 to about 7,500 g/mol, the Mw is 1,000 to about 20,000 g/mol, and the Mz is about 1400 (alternately 1700) to about 150,000 g/mol.
13. The oligomer of any of paragraphs 1-12, wherein the oligomer has no detectable melting point by DSC following storage at ambient temperature for at least 48 hours.
14. The oligomer of any of paragraphs 1-12, wherein the oligomer has a melting peak of from about 60° C. to about 130° C.
15. A homogenous process for making the propylene co-oligomer of any of the above paragraphs 1 to 14, said process having productivity of at least $4.5 \times 10^3$ g/mmol/hr, wherein the process comprises:
contacting, at a temperature of from 35° C. to 150° C., propylene, 0.1 to 70 mol % ethylene and from 0 to about 5 wt % hydrogen in the presence of a catalyst system comprising an activator and at least one metallocene compound represented by the formulae:

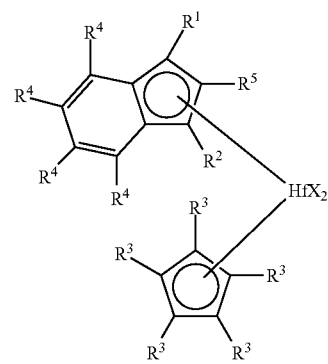

I

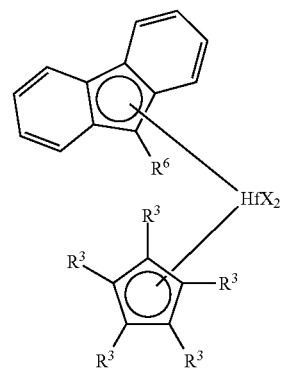

II

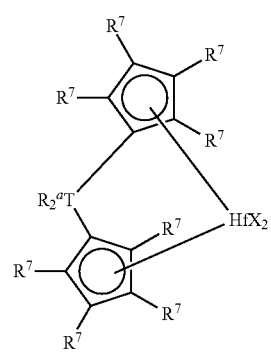

III

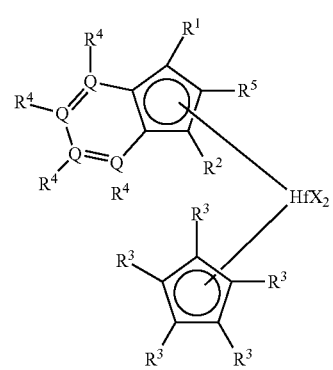

IV where

Hf is hafnium;

each X is, independently, selected from the group consisting of hydrocarbyl radicals having from 1 to 20 carbon atoms, hydrides, amides, alkoxides, sulfides, phosphides, halogens, dienes, amines, phosphines, ethers, or a combination thereof, preferably methyl, ethyl, propyl, butyl, phenyl, benzyl, chloride, bromide, iodide, (alternately two X's may form a part of a fused ring or a ring system);

each Q is, independently, carbon or a heteroatom, preferably C, N, P, S (preferably at least one Q is a heteroatom, alternately at least two Q's are the same or different heteroatoms, alternately at least three Q's are the same or different heteroatoms, alternately at least four Q's are the same or different heteroatoms);

each $R^1$ is, independently, a $C_1$ to $C_8$ alkyl group, preferably a $C_1$ to $C_8$ linear alkyl group, preferably methyl ethyl, propyl, butyl, pentyl, hexyl, heptyl or octyl, $R^1$ may the same or different as $R^2$;

each $R^2$ is, independently, a $C_1$ to $C_8$ alkyl group, preferably a $C_1$ to $C_8$ linear alkyl group, preferably methyl ethyl, propyl, butyl, pentyl, hexyl, heptyl or octyl, preferably $R^1$ and/or $R^2$ are not branched;

each $R^3$ is, independently, hydrogen, or a substituted or unsubstituted hydrocarbyl group having from 1 to 8 carbon atoms, preferably 1 to 6 carbon atoms, preferably a substituted or unsubstituted $C_1$ to $C_8$ linear alkyl group, preferably methyl ethyl, propyl, butyl, pentyl, hexyl, heptyl, octyl, provided however that at least three $R^3$ groups are not hydrogen (alternately four $R^3$ groups are not hydrogen, alternately five $R^3$ groups are not hydrogen);

each $R^4$ is, independently, hydrogen or a substituted or unsubstituted hydrocarbyl group, a heteroatom or heteroatom containing group, preferably a substituted or unsubstituted hydrocarbyl group having from 1 to 20 carbon atoms, preferably 1 to 8 carbon atoms, preferably a substituted or unsubstituted $C_1$ to $C_8$ linear alkyl group, preferably methyl ethyl, propyl, butyl, pentyl, hexyl, heptyl, octyl, substituted phenyl (such as propyl phenyl), phenyl, silyl, substituted silyl, (such as $CH_2SiR'$, where R' is a $C_1$ to $C_{12}$ hydrocarbyl, such as methyl, ethyl, propyl, butyl, phenyl);

$R^5$ is hydrogen or a $C_1$ to $C_8$ alkyl group, preferably a $C_1$ to $C_8$ linear alkyl group, preferably methyl, ethyl, propyl, butyl, pentyl, hexyl, heptyl or octyl;

$R^6$ is hydrogen or a $C_1$ to $C_8$ alkyl group, preferably a $C_1$ to $C_8$ linear alkyl group, preferably methyl, ethyl, propyl, butyl, pentyl, hexyl, heptyl or octyl;

each $R^7$ is, independently, hydrogen, or a $C_1$ to $C_8$ alkyl group, preferably a $C_1$ to $C_8$ linear alkyl group, preferably methyl ethyl, propyl, butyl, pentyl, hexyl, heptyl or octyl, provided however that at least seven $R^7$ groups are not hydrogen, alternately at least eight $R^7$ groups are not hydrogen, alternately all $R^7$ groups are not hydrogen, (preferably the $R^7$ groups at the 3 and 4 positions on each Cp ring of Formula IV are not hydrogen);

N is nitrogen;

T is a bridge, preferably, Si or Ge, preferably Si;

each $R^a$, is independently, hydrogen, halogen or a C1 to C20 hydrocarbyl, such as methyl, ethyl, propyl, butyl, pentyl, hexyl, heptyl, octyl, phenyl, benzyl, substituted phenyl, and two $R^a$ can form a cyclic structure including aromatic, partially saturated, or saturated cyclic or fused ring system;

and further provided that any two adjacent R groups may form a fused ring or multicenter fused ring system where the rings may be aromatic, partially saturated or saturated.

16. A homogenous process for making the propylene homo-oligomer of any of paragraphs 1 to 14, said process having a productivity of at least $4.5 \times 10^6$ g/mol/min, wherein the process comprises:

contacting, at a temperature of from 30° C. to 120° C., propylene, 0 mol % comonomer and from 0 to about 5 wt % hydrogen in the presence of a catalyst system comprising an activator and at least one metallocene compound represented by the formulae:

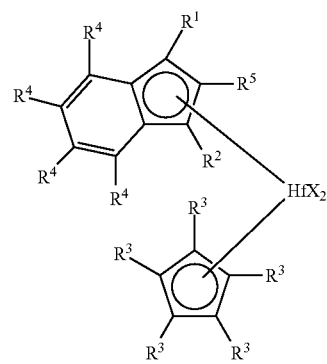

I

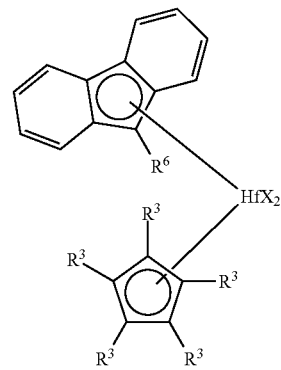

II

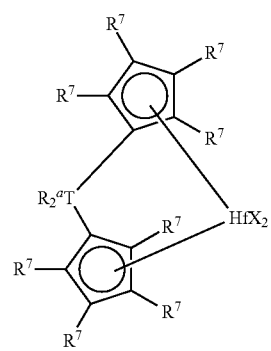

III

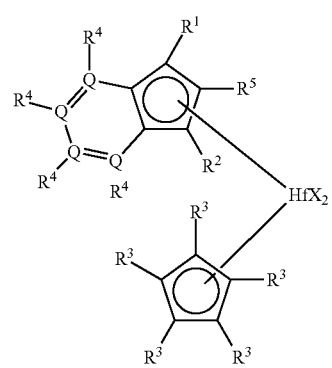

IV where

Hf is hafnium;

each X is, independently, selected from the group consisting of hydrocarbyl radicals having from 1 to 20 carbon atoms, hydrides, amides, alkoxides, sulfides, phosphides, halogens, dienes, amines, phosphines, ethers, or a combination thereof, preferably methyl, ethyl, propyl, butyl, phenyl, benzyl, chloride, bromide, iodide, (alternately two X's may form a part of a fused ring or a ring system);

each Q is, independently carbon or a heteroatom, preferably C, N, P, S (preferably at least one Q is a heteroatom, alternately at least two Q's are the same or different heteroatoms, alternately at least three Q's are the same or different heteroatoms, alternately at least four Q's are the same or different heteroatoms);

each $R^1$ is, independently, a $C_1$ to $C_8$ alkyl group, preferably a $C_1$ to $C_8$ linear alkyl group, preferably methyl ethyl, propyl, butyl, pentyl, hexyl, heptyl or octyl, $R^1$ may the same or different as $R^2$;

each $R^2$ is, independently, a $C_1$ to $C_8$ alkyl group, preferably a $C_1$ to $C_8$ linear alkyl group, preferably methyl ethyl, propyl, butyl, pentyl, hexyl, heptyl or octyl, preferably $R^1$ and/or $R^2$ are not branched;

each $R^3$ is, independently, hydrogen, or a substituted or unsubstituted hydrocarbyl group having from 1 to 8 carbon atoms, preferably 1 to 6 carbon atoms, preferably a substituted or unsubstituted $C_1$ to $C_8$ linear alkyl group, preferably methyl ethyl, propyl, butyl, pentyl, hexyl, heptyl, octyl, provided however that: 1) all five $R^3$ groups are methyl, or 2) four $R^3$ groups are not hydrogen and at least one $R^3$ group is a $C_2$ to $C_8$ substituted or unsubstituted hydrocarbyl (preferably at least two, three, four or five $R^3$ groups are a $C_2$ to $C_8$ substituted or unsubstituted hydrocarbyl);

each $R^4$ is, independently, hydrogen or a substituted or unsubstituted hydrocarbyl group, a heteroatom or heteroatom containing group, preferably a substituted or unsubstituted hydrocarbyl group having from 1 to 20 carbon atoms, preferably 1 to 8 carbon atoms, preferably a substituted or unsubstituted $C_1$ to $C_8$ linear alkyl group, preferably methyl ethyl, propyl, butyl, pentyl, hexyl, heptyl, octyl, substituted phenyl (such as propyl phenyl), phenyl, silyl, substituted silyl, (such as $CH_2SiR'$, where R' is a $C_1$ to $C_{12}$ hydrocarbyl, such as methyl, ethyl, propyl, butyl, phenyl);

$R^5$ is hydrogen or a $C_1$ to $C_8$ alkyl group, preferably a $C_1$ to $C_8$ linear alkyl group, preferably methyl, ethyl, propyl, butyl, pentyl, hexyl, heptyl or octyl;

$R^6$ is hydrogen or a $C_1$ to $C_8$ alkyl group, preferably a $C_1$ to $C_8$ linear alkyl group, preferably methyl, ethyl, propyl, butyl, pentyl, hexyl, heptyl or octyl;

each $R^7$ is, independently, hydrogen, or a $C_1$ to $C_8$ alkyl group, preferably a $C_1$ to $C_8$ linear alkyl group, preferably methyl ethyl, propyl, butyl, pentyl, hexyl, heptyl or octyl, provided however that at least seven $R^7$ groups are not hydrogen, alternately at least eight $R^7$ groups are not hydrogen, alternately all $R^7$ groups are not hydrogen, (preferably the $R^7$ groups at the 3 and 4 positions on each Cp ring of Formula IV are not hydrogen);

N is nitrogen;

T is a bridge, preferably, Si or Ge, preferably Si;

each $R^a$, is independently, hydrogen, halogen or a C1 to C20 hydrocarbyl, such as methyl, ethyl, propyl, butyl, pentyl, hexyl, heptyl, octyl, phenyl, benzyl, substituted phenyl, and two $R^a$ can form a cyclic structure including aromatic, partially saturated, or saturated cyclic or fused ring system; and further provided that any two adjacent R groups may form a fused ring or multicenter fused ring system where the rings may be aromatic, partially saturated or saturated.

17. The process of paragraph 15 or 16, wherein the activator comprises one or more non-coordinating anions.

18. The process of paragraph 15, 16, or 17 wherein the catalyst system comprises one or more of (pentamethylcyclopentadienyl)(1,3 dimethylindenyl)hafnium)dimethyl, and (pentamethylcyclopentadienyl)(1,3 dimethylindenyl) hafnium)dichloride.

19. The process of paragraph 15 or 17, wherein the catalyst system comprises one or more of (1,3-Dimethylindenyl) (pentamethylcyclopentadienyl)Hafniumdimethyl, (1,3,4, 7-Tetramethylindenyl)(pentamethylcyclopentadienyl) Hafniumdimethyl, (1,3-Dimethylindenyl) (tetramethylcyclopentadienyl)Hafniumdimethyl, (1,3-Diethylindenyl)(pentamethylcyclopentadienyl) Hafniumdimethyl, (1,3-Dipropylindenyl) (pentamethylcyclopentadienyl)Hafniumdimethyl, (1-Methyl,3-propyllindenyl)(pentamethylcyclopentadienyl)Hafniumdimethyl, (1,3-Dimethylindenyl)(tetramethylpropylcyclopentadienyl)Hafniumdimethyl, (1,2,3-Trimethylindenyl)(pentamethylcyclopentadienyl) Hafniumdimethyl, (1,3-Dimethylbenzindenyl) (pentamethylcyclopentadienyl)Hafniumdimethyl, (2,7-Bis t-butylfluorenyl)(pentamethylcyclopentadienyl) Hafniumdimethyl, (9-Methylfluorenyl)(pentamethylcyclopentadienyl)Hafniumdimethyl, (2,7,9-Trimethylfluorenyl)(pentamethylcyclopentadienyl)Hafniumdimethyl, μ-Dihydrosilyl(bis tetramethylcyclopentadienyl)Hafniumdimethyl, μ-Dihydrosilyl(bis tetramethylcyclopentadienyl)Hafniumdimethyl, μ-Dimethylsilyl(tetramethylcyclopentadienyl)(3-propyltrimethylcyclopentadienyl) Hafniumdimethyl, μ-Dicyclopropylsilyl(bis tetramethylcyclopentadienyl)Hafnium dimethyl. (1,3-Dimethylindenyl)(pentamethylcyclopentadienyl)Hafniumdihalide, (1,3,4,7-Tetramethylindenyl)(pentamethylcyclopentadienyl)Hafniumdihalide, (1,3-Dimethylindenyl)(tetramethylcyclopentadienyl)Hafniumdihalide, (1,3-Diethylindenyl)(pentamethylcyclopentadienyl)Hafniumdihalide, (1,3-Dipropylindenyl)(pentamethylcyclopentadienyl) Hafniumdihalide, (1-Methyl,3-propyllindenyl)(pentamethylcyclopentadienyl)Hafniumdihalide, (1,3-Dimethylindenyl)(tetramethylpropylcyclopentadienyl) Hafniumdihalide, (1,2,3-Trimethylindenyl) (pentamethylcyclopentadienyl)Hafniumdihalide, (1,3-Dimethylbenzindenyl)(pentamethylcyclopentadienyl) Hafniumdihalide, (2,7-Bis t-butylfluorenyl) (pentamethylcyclopentadienyl)Hafniumdihalide, (9-Methylfluorenyl)(pentamethylcyclopentadienyl) Hafniumdihalide, (2,7,9-Trimethylfluorenyl)(pentamethylcyclopentadienyl)Hafniumdihalide, μ-Dihydrosilyl(bis tetramethylcyclopentadienyl)Hafniumdihalide, μ-Dihydrosilyl(bis tetramethylcyclopentadienyl)Hafniumdihalide, μ-Dihalidesilyhtetramethylcyclopentadienyl)(3-propyltrimethylcyclopentadienyl) Hafniumdihalide, and μ-Dicyclopropylsilyl(bis tetramethylcyclopentadienyl) Hafnium dihalide.

20. The process of paragraph 16 or 17, wherein the catalyst system comprises one or more of (1,3-Dimethylindenyl) (pentamethylcyclopentadienyl)Hafniumdimethyl, (1,3,4, 7-Tetramethylindenyl)(pentamethylcyclopentadienyl) Hafniumdimethyl, (1,3-Diethylindenyl) (pentamethylcyclopentadienyl)Hafniumdimethyl, (1,3-Dipropylindenyl)(pentamethylcyclopentadienyl) Hafniumdimethyl, (1-Methyl,3-propyllindenyl) (pentamethylcyclopentadienyl)Hafniumdimethyl, (1,2,3-Trimethylindenyl)(pentamethylcyclopentadienyl) Hafniumdimethyl, (1,3-Dimethylbenzindenyl) (pentamethylcyclopentadienyl)Hafniumdimethyl, (2,7-Bis t-butylfluorenyl)(pentamethylcyclopentadienyl) Hafniumdimethyl, (9-Methylfluorenyl)(pentamethylcyclopentadienyl)Hafniumdimethyl, (2,7,9-Trimethylfluorenyl)(pentamethylcyclopentadienyl)Hafniumdimethyl, (1,3-Dimethylindenyl)(pentamethylcyclopentadienyl) Hafniumdihalide, (1,3,4,7-Tetramethylindenyl)(pentamethylcyclopentadienyl)Hafniumdihalide, (1,3-Diethylindenyl)(pentamethylcyclopentadienyl)Hafniumdihalide, (1,3-Dipropylindenyl)(pentamethylcyclopentadienyl) Hafniumdihalide, (1-Methyl,3-propyllindenyl)(pentamethylcyclopentadienyl)Hafniumdihalide, (1,2,3-Trimethylindenyl)(pentamethylcyclopentadienyl) Hafniumdihalide, (1,3-Dimethylbenzindenyl)(pentamethylcyclopentadienyl)Hafniumdihalide, (2,7-Bis t-butylfluorenyl)(pentamethylcyclopentadienyl)Hafniumdihalide, (9-Methylfluorenyl)(pentamethylcyclopentadienyl)Hafniumdihalide, and (2,7,9-Trimethylfluorenyl)(pentamethylcyclopentadienyl)Hafniumdihalide.

21. The process of any of paragraphs 15 to 20, further comprising functionalizing the propylene oligomer.

22. The process of any of paragraphs 15 to 20, further comprising functionalizing the propylene oligomer with succinic acid, maleic acid, maleic anhydride or combinations thereof.

EXAMPLES

The foregoing discussion can be further described with reference to the following non-limiting examples.

Product Characterization

Products were characterized by $^1$H NMR and $^{13}$C NMR as follows:

$^{13}$C NMR $^{13}$C NMR data was collected at 120° C. in a 10 mm probe using a Varian spectrometer with a $^1$Hydrogen frequency of at least 400 MHz. A 90 degree pulse, an acquisition time adjusted to give a digital resolution between 0.1 and 0.12 Hz, at least a 10 second pulse acquisition delay time with continuous broadband proton decoupling using swept square wave modulation without gating was employed during the entire acquisition period. The spectra were acquired using time averaging to provide a signal to noise level adequate to measure the signals of interest. Samples were dissolved in tetrachloroethane-d$_2$ at concentrations between 10 to 15 wt % prior to being inserted into the spectrometer magnet.

Prior to data analysis spectra were referenced by setting the chemical shift of the (—CH$_2$—)$_n$ signal where n>6 to 29.9 ppm.

Chain ends for quantization were identified using the signals shown in the table below. N-butyl and n-propyl were not reported due to their low abundance (less than 5%) relative to the chain ends shown in the table below.

| Chain End | $^{13}$CNMR Chemical Shift |
| --- | --- |
| P~i-Bu | 23-5 to 25.5 and 25.8 to 26.3 ppm |
| E~i-Bu | 39.5 to 40.2 ppm |
| P~Vinyl | 41.5 to 43 ppm |
| E~Vinyl | 33.9 to 34.4 ppm |

$^1$H NMR $^1$H NMR data was collected at either room temperature or 120° C. (for purposes of the claims, 120° C. shall be used) in a 5 mm probe using a Varian spectrometer with a $^1$Hydrogen frequency of at least 400 MHz. Data was recorded using a maximum pulse width of 45° C., 8 seconds between pulses and signal averaging 120 transients. Spectral signals were integrated and the number of unsaturation types per 1000 carbons was calculated by multiplying the different groups by 1000 and dividing the result by the total number of carbons. Mn was calculated by dividing the total number of unsaturated species into 14,000.

The chemical shift regions for the olefin types are defined to be between the following spectral regions.

| Unsaturation Type | Region (ppm) | Number of hydrogens per structure |
| --- | --- | --- |
| Vinyl | 4.95-5.10 | 2 |
| Vinylidene | 4.70-4.84 | 2 |
| Vinylene | 5.31-5.55 | 2 |
| Trisubstituted | 5.11-5.30 | 1 |

The populations of olefin unsaturations found in the products by $^1$H NMR are summarized in Table 3. In this table, the vinyl population, as a percentage of total unsaturation, is provided as well, along with the number average molecular weight calculated by assuming one unsaturation per chain and degree of polymerization, or average number of propylene units per chain. For the propylene oligomer products, the % vinyl ranges from ~0 (comparative examples A and B catalysts) to as high as ~98% (F). Regardless of activator, the less sterically encumbered A, B catalysts (comparative examples) did not produce significant vinyl populations, and the metallocenes D, G and H also produce products with low allylic vinyl content (10 to 42%). In the case of E, the activator appears to impact the chain termination pathway. In the case of F runs, high allylic vinyl populations were attained with both 1 and 4 activators, although allylic vinyl population decreased modestly with increasing polymerization temperature. Temperature played a role in the % vinyl for E but less so for F. Where impact was observed, it was opposite to using bridged, chiral metallocenes.

Glass Transition Temperature (Tg) was measured by DSC as described above.

Viscosity was measured at 35° C. using a Brookfield viscometer.

Refractive Index was measured at 25° C. with 589 nm Na line.

Materials

The following metallocenes were used:

A=bis(1-methyl,3-n-butylcyclopentadienyl)zirconium dimethyl;
B=dimethylsilyl bis(4,5,6,7-tetrahydroindenyl)zircomium dimethyl;
C=dimethylsilyl bis(indenyl)hafnium dimethyl;
D=(tetramethylcyclopentadienyl)(1,3-dimethylindenyl)zirconium dimethyl;
E=(tetramethylcyclopentadienyl)(1,3-dimethylindenyl) hafnium dimethyl;
F=(pentamethylcyclopentadienyl)(1,3-dimethylindenyl) hafnium dimethyl;
G=(tetramethylcyclopentadienyl)(1-isopropylindenyl) hafnium dimethyl;
H=(tetramethylcyclopentadienyl)(1-isopropyl,3-n-propylindenyl)hafnium dimethyl; and
J=dimethylsilyl bis(2-methyl,4-phenylindenyl)zirconium dimethyl.

Several ionic activators and one supported ionic activator were used to activate the metallocenes. The ionic activators used were:

1=dimethylanilinium perfluorotetraphenylborate,
2=4-tert-butylanilinium bis(pentafluorophenyl)bis(perfluoro-2-napthyl)borate,
3=4-tert-butylanilinium (pentafluorophenyl)tris(perfluoro-2-napthyl)borate, 4=dimethylanilinium tetrakis(perfluoro-2-napthyl)borate,
5=dimethylanilinium tetrakis(3,5 (pentafluorophenyl)perfluorophenylborate); and
6=tris-perfluorophenyl boron.

Catalyst Compound Synthesis: Typical dry-box procedures for synthesis of air-sensitive compounds were followed. Solvents were purchased from Aldrich and dried over 2A sieves. Indene was purchased from Aldrich and pentamethylcyclopentadiene was purchased from Norquay. Metallocenes A, B and C were purchased from Boulder scientific or Albemarle. The activators were purchased from Albemarle or Grace Davison.

Catalyst F: $(CpMe_5)(1,3-Me_2C_9H_5)HfMe_2$ $LiC_9H_7$ was generated in $Et_2O$ (−35° C.) by the reaction of 29 g indene (0.25 mol) with 1 equivalent of n-BuLi (10 M, hexane) added slowly. $LiC_9H_7$ was isolated by reduction of the ether solution, addition of hexane and filtration over a medium glass frit. The product was washed with additional hexane (2×40 mL). $LiC_9H_7$ was dissolved in $Et_2O$, cooled to −35° C. and reacted with excess MeI (0.375 mol, 47.6 g). After 2 hours the reaction mixture was warmed to ambient temperature. $1-MeC_9H_7$ was isolated as a colorless liquid by aqueous work-up and ether extractions. Similarly 1,3-$Me_2C_9H_6$ was synthesized by lithiation of $MeC_9H_7$, methylation with MeI and aqueous work-up. $[Li][1,3-Me_2C_9H_5]$ was synthesized by reaction of $1,3-Me_2C_9H_6$ in hexane with excess nBuLi (1.1 equiv) for 12 hours. The white solid was filtered and washed with additional hexane and dried in vacuo to yield pure $[Li][1,3-Me_2C_9H_5]$, B (14.5 g). $^1H$ NMR (THF-$d_8$, 300 MHz) δ ppm; 7.25-7.10 (m, $C_6H_4$, 2H), 6.45-6.30, $C_6H_4$, 2H), 6.10 (s, 2-indenyl proton, 1H), 2.35 (s, $1,3Me_2C_9H_5$, 6 H).

$CpMe_5HfCl_3$ (Crowther, D.; Baenziger, N.; Jordan, R.; J. Journal of the American Chemical Society (1991), 113(4), 1455-1457) (10.4 g) was reacted with $[Li][1,3-Me_2C_9H_5]$ (3.7 g, 24.8 mmol) in $Et_2O$ (100 ml) for 12 hours. The yellow product was collected by filtration over a glass frit and dried to yield crude $(CpMe_5)(1,3-Me_2C_9H_5)HfCl_2$ (8.6 g) as a mixture with LiCl.
$^1H$ NMR ($CD_2Cl_2$, 300 MHz) δ ppm; 7.58-7.11 (m, $C_6H_4$), 6.17 (s, 2-indenyl proton, 2.32 (s, $1,3Me_2C_9H_5$), 2.09 (s, $CpMe_5$).

Crude $(CpMe_5)(1,3-Me_2C_9H_5)HfCl_2$ (2.5 g) was slurried in toluene (100 ml) and reacted with MeMgI (4.2 g, 2.1 equiv, 3.0 M in $Et_2O$). The reaction mixture was heated to 80° C. for 3 hours. After cooling the volatiles were removed in vacuo to yield a solid which was extracted with hexane (4×40 mL). Hexane was removed from the combined extractions to yield solid yellow $(CpMe_5)(1,3-Me_2C_9H_5)HfMe_2$, E (1.6 g). $^1H$ NMR($C_6D_6$, 300 MHz) δ ppm; 7.55-7.48 (m, $C_6H_4$, 2H), 7.20-7.16 (m, $C_9H_5$, 3H), 2.00 (s, $1,3Me_2C_9H_5$, 6H), 1.76 (s, $CpMe_5$, 15H), −0.95 (s, Hf-Me, 6H).

Catalyst D: $(CpMe_4)(1,3-Me_2C_9H_5)ZrMe_2$ $ZrCl_4$ (36 g) was slurried in $CH_2Cl_2$ (200 mL) and then reacted with $Me_2S$ (19.2 g) for 1 hour. $CpMe_4HSiMe_3$ (34 g) was added slowly to the reaction mixture. Yellow solid began to precipitate after several hours and was filtered to yield a first crop of 21.3 g of light yellow solid product. $(CpMe_4H)ZrCl_3.(SMe_2)_x$ $^1H$ NMR ($CD_2Cl_2$, 300 MHz) δ ppm: 6.05 (s, $CpMe_4H$), 2.6 (br s, MeS), 2.27 (s, $CpMe_4$), 2.20 (s, $CpMe_4$).

$(CpMe_4H)ZrCl_3$ (15.0 g) was slurried in $Et_2O$ (250 mL) and reacted with $[Li][1,3-Me_2C_9H_5]$ (7.5 g) for 16 hours. The reaction product was filtered over a glass frit, washed with $CH_2Cl_2$ and dried in vacuo. All the solid product (ca 22 g) was slurried in $Et_2O$ (200 mL) and reacted with MeMgI (38 g 3 M in $Et_2O$). After 4 hours dimethoxyethane (6.8 g) was added and the reaction mixture filtered. Additional $Et_2O$ was used to extract the solid residue. The filtrates were reduced and cooled to −35° C. An off-white solid product was filtered and dried in vacuo (14.8 g). $(CpMe_4)(1,3-Me_2C_9H_5)ZrMe_2$.
$^1H$ NMR ($CD_2Cl_2$, 500 MHz) δ ppm; 7.35, 7.05 (m, $C_9H_5$), 5.51 (s, $C_9H_5$), 4.83 (s, $CpMe_4H$), 2.17 (s, $Me_2C_9H_5$), 1.79, 1.70 (s, $CpMe_4H$), −1.31 ZrMe.

Catalyst E: $(CpMe_4)(1,3-Me_2C_9H_5)HfMe_2$ $HfCl_4$ (31 g) was slurried in $CH_2Cl_2$ (200 mL) and reacted slowly with $CpMe_4HSiMe_3$ for several hours. The reaction mixture was filtered, reduced in volume and hexane (80 mL) was added. The filtrate was cooled to −35° C. The off-white product was collected and dried in vacuo. $(CpMe_4H)HfCl_3$ (8.0 g) was dissolved in $Et_2O$ (150 mL) and reacted with $[Li][1,3-Me_2C_9H_5]$ (2.8 g). After 1 hour the volatiles were removed and the crude reaction mixture extracted with $CH_2Cl_2$ (2×60 mL). The filtrate was reduced in vacuo to a light yellow solid product (7.2 g). All $(CpMe_4)(1,3-Me_2C_9H_5)HfCl_2$ (7.2 g) was slurried in toluene (200 mL) and reacted with 2 equivalents of MeMgBr (3 M in $Et_2O$). The reaction mixture was heated to 90° C. for 6 hours. The mixture was cooled to room temperature and dimethoxyethane (3 ml) was added. The volatiles were removed, the residue extracted with $CH_2Cl_2$ and the filtrates were reduced in vacuo. The product was collected after cooling to −35° C. (2.85 g). $(CpMe_4)(1,3-Me_2C_9H_5)HfMe_2$ $^1H$ NMR ($CD_2Cl_2$, 500 MHz) δ ppm; 7.35, 7.06 (m, $C_9H_5$), 5.50 (s, $C_9H_5$), 4.89 (s, $CpMe_4H$), 2.18 (s, $Me_2C_9H_5$), 1.79, 1.76 (s, $CpMe_4H$), −1.49 HfMe.

Catalyst H: (tetramethylcyclopentadienyl)(1-isopropyl,3-propyl-$C_9H_6$)$HfMe_2$ 1-isopropyl, 3-propyl-$C_9H_6$ was synthesized by reaction of 1-isopropylindenyl lithium with propyl bromide in $Et_2O$. The lithium salt is synthesized from BuLi in $Et_2O$. $[Li][1-isopropyl, 3-propyl-C_9H_5]$ (2.1 g) was dissolved in $Et_2O$ (60 mL) and reacted with $(CpMe_4H)HfCl_3$ (4.0 g). MeMgI (2 equivalents) were added to the reaction mixture, 60 ml toluene added and the reaction was heated to 90° C. After 2 hours the reaction was cooled, volatiles removed and the dimethyl product extracted with hexane. The product was obtained as an amber oil (3.8 g). $^1H$ NMR($C_6D_6$, 300 MHz) δ ppm; 7.48 (d), another doublet partially obscured under solvent 7.02 (m), 5.53 (s), 4.72 (s), 3.25 (p), 2.72 (m), 2.31 (m), 2.83, 2.77, 2.74, 2.73 (s), 1.22 (d), 1.07 (d), −0.73(s, Hf-Me), −1.29 (s, Hf-Me).

Catalyst G: $(CpMe_4)(1-iC_3H_7—C_9H_5)HfMe_2$

1-Isopropylindenyl lithium (Bradley et al, OM, 2004, 23, 5332) (2.0 g) was slurried in $Et_2O$ (100 mL) and reacted with $(CpMe_4H)HfCl_3$ (5.0 g) for 12 hours. The solid product was filtered and washed with hexane (3.7 g). $(CpMe_4)(1-iC_3H_7—C_9H_5)HfCl_2$ $^1H$ NMR ($C_6D_6$, 300 MHz) δ ppm; 7.55, 7.41 (d), 6.95 (p), 6.22 (d), 5.51 (d), 4.96 (s), 3.72 (p), 1.93, 1.92, 1.83, 1.64 (s), 1.34, 1.11 (d).

The dichloride was slurried in toluene (50 mL) and reacted with 2 equivalents of MeMgI (3 M in $Et_2O$). The reaction was heated to 90° C. for 2 hours and then cooled. The volatiles were removed. The crude mixture was extracted with hexane (2×40 mL), filtered and filtrate reduced to solid product in vacuo (3.1 g). $^1$H NMR(C$_6$D$_6$, 300 MHz) δ ppm; −0.52, −1.46 Hf-Me.

TEAL-SiO$_2$: SiO$_2$ Davison 948 calcined at 600° C. was slurried in hexane (30 mL) and reacted with Triethylaluminum (10 mL, 1.9 M in toluene) for 12 hours. The solid was filtered and washed with hexane (2×20 mL). After drying in vacuo the yield was 10.75 g TEAL-SiO$_2$.

Catalyst I

TEAL-SiO$_2$ (2.0 g) was slurried in toluene (30 mL) and reacted with Triphenylcarbonium tetrakisperfluorophenyl borate (142 mg, Grace Davison) for 10 minutes. Metallocene E (56 mg) was added as a solution in toluene (5 mL) to the slurry and allowed to react for 12 hours. The supported catalyst was filtered, washed with hexane and dried in vacuo.

Catalyst K

Similar to Catalyst I, Metallocene E was supported as described above except that 3.8 g TEAL-SiO$_2$, 215 mg of ionic activator 1, and 114 mg of metallocene E were used.

Polymerizations

Propylene oligomer batch or continuous polymerizations were carried out for this study using a 2 L stirred autoclave reactor are described in Table 1. Catalyst solutions were prepared in a dry nitrogen purged Vacuum Atmospheres dry box by adding nearly equimolar (typically 1.00:1.05) quantities of metallocene and activator to 4 mL dry toluene in a 10 mL glass vial. The mixture was stirred for several minutes and then transferred to a clean, oven dried catalyst tube. An example of the basic polymerization procedure follows: 2 mL of 25 wt % tri-n-octyl-aluminum (0.037 g Al) in hexanes as scavenger and 100 mL propylene were added to the reactor. Next the reactor was heated to the selected polymerization temperature and catalyst/activator was flushed from the catalyst tube into the reactor with 100 mL propylene. Additional propylene was optionally added for a total of up to 1000 mL. In some cases, hydrogen was also added from a ballast tank (see Table 2A). Hydrogen partial pressure was as high as 50 psig at the start of the run. Polymerization was carried out for 10 to 60 minutes, and then the reactor was cooled, depressurized, and opened. At this point the collected product typically contained some residual monomer. The residual monomer concentration in the product was initially reduced by "weathering." In many cases the sample was heated in the oven under nitrogen purge or for a short time with applied vacuum. Some of the lowest molecular weight oligomer product may be lost along with the residual monomer. In some cases, residual monomer is still detected in the product in $^1$H NMR spectra recorded at 30° C. (but is not detected when spectra are recorded at 120° C.). In the Tables below Polig means propylene oligomer, EP means propylene-ethylene oligomer, T$_p$ means polymerization temperature, P-time means polymerization time, Cat means catalyst, Act means activator, DP means degree of polymerization.

TABLE 1

Summary of Propylene Polymerizations

| Example | Product | Cat | Act | Cat/Act (mg/mg) | Tp (° C.) | P-time (min) | Yield (g) | Additional C3 ** |
|---|---|---|---|---|---|---|---|---|
| 1 # | Polig | A | 4 | 30/60 | 90 | 10 | 25 | *** |
| 2 # | Polig | B | 4 | 10/25 | 90 | 7 | 110 | *** |
| 3 # | Polig | A | 4 | 30/60 | 140 | 10 | 25 | *** |
| 4 # | Polig | C | 4 | 10/25 | 140 | 8 | 160 | *** |
| 5 # | Polig | B | 4 | 4/12 | 145 | 7 | 140 | *** |
| 6 # | Polig | B | 1 | 6/15 | 152 | 5 | 47 | *** |
| 7 # | Polig | B | 1 | 6/15 | 130 | 10 | 30 | *** |
| 8 | Polig | D | 4 | 6/13.1 | 132 | 10 | 5.7 | *** |
| 9 | Polig | E | 4 | 10/25.7 | 132 | 10 | 19 | *** |
| 10 | Polig | E | 4 | 10/25.7 | 100 | 12 | 31.9 | 100 |
| 11 | Polig | E | 4 | 10/25.7 | 80 | 12 | 52.5 | 100 |
| 12 | Polig | E | 4 | 10/25.7 | 80 | 27 | 142 | 400 |
| 13 | Polig | E | 4 | 10/25.7 | 60 | 10 | 65 | *** |
| 14 | Polig | E | 4 | 12/30.8 | 75 | 40 | 242 | 500 |
| 21 | Polig | E | 1 | 10/17.9 | 132 | 10 | 17.9 | *** |
| 22 | Polig | E | 1 | 10/17.9 | 80 | 12 | 46.2 | 100 |
| 23 | Polig | E | 4 | 10/25.7 | 80 | 27 | ~127 | 300 |
| 24 | Polig | D | 4 | 10/31.5 | 80 | 10 | 8.9 | 150 |
| 26 | Polig | E | 6 | 10/11.5 | 80 | 30 | 0 | *** |
| 25 ^ | Polig | K(150 mg) |  |  | 80 | 30 | 9.8 | 250 |
| 28 ^ | Polig | I(210 mg) |  |  | 60 | 30 | 14.9 | *** |
| 27 | Polig | E | 6 | 10/11.5 | 132 | 30 | 0 | *** |
| 30 | Polig | E | 5 | 10/45.7 | 80 | 30 | 162 | 450 |
| 31 | Polig | E | 2 | 10/23.1 | 80 | 30 | 112 | 350 |
| 32 | Polig | E | 3 | 10/25.7 | 80 | 30 | 112 | 250 |
| 36 | Polig | E | 1 | 10/17.9 | 45 | 30 | 130 | *** |
| 37 | Polig | H | 4 | 10/25 | 80 | 30 | 13.2 | 200 |
| 38 | Polig | F | 4 | 10/25 | 80 | 30 | 46.2 | 250 |
| 39 | Polig | G | 4 | 10/22.7 | 80 | 25 | 70 | 150 |
| 40 | Polig | G | 4 | 10/22.7 | 100 | 30 | 55.7 | 70 |
| 41 | Polig | G | 4 | 10/22.7 | 132 | 30 | 16.2 | 40 |
| 42 | Polig | E | 4 | 10/25.7 | 38 | 20 | ~200 | *** |
| 44 | Polig | E | 4 | 10/25 | 60 | 30 | ~75 | *** |
| 45 | Polig | E | 4 | 10/25 | 37 | 30 | ~85 | *** |
| 46 | Polig | E | 4 | 10/25 | 100 | 30 | 36.7 | 80 |
| 47 | Polig | E | 4 | 10/25 | 132 | 30 | ~10 | *** |
| 48 | Polig | E | 1 | 10/18 | 60 | 30 | ~110 | *** |
| 49 | Polig | E | 1 | 10/18 | 80 | 30 | ~70 | 280 |
| 50 | Polig | E | 4 | 10/25 | 60 | 180 | ~200 | *** |
| 51 | Polig | E | 1 | 10/18 | 60 | 120 | ~220 | *** | comparative,
^ supported,
** Additional propylene added,
*** Continuous run using continuous propylene feed from day tank Propylene-ethylene co-oligomerizations, carried out for this study using a 2 L stirred autoclave reactor, are described in Table 2. Catalyst solutions were prepared in a dry nitrogen purged Vacuum Atmospheres dry box by adding nearly equimolar (typically 1.00:1.05) quantities of metallocene and activator to 4 mL dry toluene in a 10 mL glass vial. The mixture was stirred for several minutes and then transferred to a clean, oven dried catalyst tube. An example of the basic polymerization procedure follows: 2 mL of 25 wt % tri-n-octyl-aluminum in hexanes as scavenger and 300 mL propylene were added to the reactor. Next the reactor was heated to appropriate polymerization temperature and catalyst/activator was flushed from the catalyst tube into the reactor with an additional 300 mL propylene. Ethylene was then added continuously throughout the reaction at partial pressures from less than 5 psi up to 220 psi. After a pre-determined reaction time, the reactor was cooled, depressurized, and opened. At this point the collected product typically contained some residual monomer. The residual monomer concentration in the product was initially reduced by "weathering." In many cases the sample was heated in the oven under nitrogen purge or for a short time with applied vacuum. Some of the lowest molecular weight oligomer product may be lost along with the residual monomer. Note that catalyst productivities are 28 to 678 times higher than the productivities reported by in *Macromolecules* 2008 41, 559-567.

TABLE 2

Summary of Propylene-Ethylene Copolymerizations

| Example | Catalyst/Activator | Mole metallocene [a] | $T_p$, °C. | Psig $C_2^=$ | Time, min | Yield, g | Productivity, g/mmol/hr |
|---|---|---|---|---|---|---|---|
| 33 | E/4 | 2.13E−05 | 65 | 20 | 10 | 320 | 90,122 |
| 35 | E/4 | 4.26E−06 | 60 | 40 | 20 | 127 | 89,526 |
| 52 | F/4 | 8.26E−06 | 60 | 40 | 20 | 240 | 87,297 |
| 53 | F/4 | 8.26E−06 | 65 | 30 | 10 | 128 | 92,838 |
| 54 | F/4 | 4.13E−06 | 60 | 20 | 10 | 178 | 258,206 |
| 55 | F/1 | 2.06E−06 | 58 | <5 | 30 | 95 | 92,055 |
| 56 | F/1 | 2.06E−06 | 70 | <5 | 30 | 87 | 84,303 |
| 57 | F/1 | 6.19E−06 | 70 | 10 | 60 | 80 | 12,920 |
| 58 | F/1 | 8.26E−06 | 68 | 30 | 10 | 158 | 114,597 |
| 59 | F/1 | 4.13E−06 | 65 | 50 | 10 | 95 | 137,806 |
| 60 | F/1 | 2.07E−06 | 55 | 220 | 10 | 108 | 313,329 |
| 61 | F/1 | 4.15E−06 | 65 | 50 | 5 | 46 | 133,455 |

[a] in all cases, slight molar excess (~5-10 mole %) of activator used with metallocene.

TABLE 2A

Propylene Polymerizations with Catalyst F in the Presence of Hydrogen

| Ex | Act | Cat/Activator (mg/mg) | $H_2$, psi | Tp. (C) | Time (min) | Yield (g) | Productivity g/mmol/hr |
|---|---|---|---|---|---|---|---|
| 62 | 4 | 10/25 | 7 | 80 | 10 | 342 | 39768 |
| 63 | 4 | 5/12.5 | 7 | 27 | 60 | 348 | 13489 |
| 64 | 4 | 4/10 | 7 | 60 | 30 | 225 | 21803 |
| 65 | 4 | 4.5/11.25 | 7 | 40 | 45 | 428 | 24579 |
| 66 | 1 | 5/9 | 7 | 29 | 50 | 525 | 33915 |
| 67 | 1 | 2/3.5 | 7 | 60 | 60 | 165 | 22841 |
| 68 | 1 | 6/10.4 | 7 | 45 | 30 | 487 | 45375 |
| 69 | 1 | 2/3.5 | 7 | 40 | 10 | 1.5 | 2180 |
| 70 | 1 | 2/3.5 | 50 | 40 | 5 | 2.3 | 6689 |
| 71 | 1 | 4/7 | 7 | 50 | 10 | 140 | 101740 |
| 72 | 1 | 4/7 | 22 | 45 | 10 | 202 | 146770 |
| 73 | 1 | 4/7 | 50 | 42 | 5 | 30 | 43622 |
| 74 | 1 | 4/7 | 50 | 47 | 30 | 325 | 78731 |

TABLE 3

Characterization Data for Propylene Oligomers

| Example | % Vinyls* | DP* | Mn* | Tg (°C.) | Viscosity at 35° C. (cps) | Refractive Index |
|---|---|---|---|---|---|---|
| 1 | 3.35 | 12.55 | 526.91 | | | |
| 2 | 5.5 | 107.5 | 4516 | | | |
| 3 | 1.50 | 6.57 | 275.92 | | | |
| 4 | 28.7 | 86.1 | 3618 | | | |
| 5 | 12.6 | 24.2 | 1017 | | | |
| 6 | 1.94 | 6.54 | 274.51 | | | |
| 7 | 1.64 | 6.93 | 291.18 | | | |
| 8 | 14.19 | 8.23 | 345.51 | | | |
| 9 | 25.03 | 4.34 | 182.43 | | | 1.4240 |
| 10 | 41.47 | 6.89 | 289.26 | | 3.5 | |
| 11 | 57.17 | 8.95 | 375.94 | | | |
| 12 | 55.74 | 9.01 | 378.28 | | 16.0 | |
| 13 | 73.30 | 26.97 | 1132.69 | −37.3 | | |
| 14 | 69.63 | 14.40 | 604.75 | | | |
| 21 | 30.75 | 3.54 | 148.48 | | | |
| 22 | 54.24 | 7.80 | 327.72 | | 37.3 | 1.4489 |
| 23 | 60.88 | 8.46 | 355.15 | | | 1.4534 |
| 24 | 24.72 | 46.04 | 1933.70 | −56.9 | | |
| 25 | 54.11 | 9.05 | 379.92 | | | |
| 28 | 63.3 | 17.48 | 734.1 | | | |
| 29 | 16.1 | 45.8 | 1923 | | | |
| 30 | 55.52 | 8.52 | 357.69 | | | |
| 31 | 57.49 | 8.54 | 358.70 | | | |
| 32 | 60.45 | 9.33 | 391.83 | | | |
| 36 | 62.37 | 68.17 | 2862.99 | −16.7 | | |
| 37 | 10.68 | 8.07 | 338.90 | | | |
| 38 | 97.20 | 4.62 | 194.04 | | | 1.4252 |
| 39 | 42.16 | 7.61 | 319.42 | | | |
| 40 | 27.06 | 4.68 | 196.63 | | | 1.4298 |
| 41 | 15.14 | 3.59 | 150.81 | | | |
| 42 | 74.12 | 106.5 | 4472.84 | | | |
| 44 | 97.48 | 7.12 | 299.02 | | | |
| 45 | 97.61 | 24.12 | 1013.02 | | | |
| 46 | 95.02 | 4.31 | 181.21 | | | 1.4367 |
| 47 | 88.73 | 3.79 | 159.25 | | | |
| 48 | 97.49 | 8.52 | 357.87 | | | |
| 49 | 97.85 | 4.68 | 196.41 | | | 1.4205 |
| 50 | 96.24 | 8.14 | 341.96 | | | |
| 51 | 97.13 | 8.24 | 346.28 | | | 1.4422 |
| 62 | 97.1 | 6.31 | 265 | | | |
| 63 | 96.5 | 22.49 | 945 | | | |
| 64 | 96.7 | 6.55 | 275 | | | |
| 65 | 98.2 | 13.59 | 570 | | | |
| 66 | 97.2 | 19.97 | 838 | | | |
| 67 | 98.0 | 6.21 | 261 | | | |
| 68 | 97.4 | 10.31 | 433 | | | |
| 71 | 98.0 | 6.79 | 285.4 | | | |
| 72 | 98.2 | 7.52 | 315.7 | | | |
| 73 | 96.7 | 10.56 | 443.5 | | | |
| 74 | 97.4 | 9.07 | 380.8 | | | |

% Vinyls = % allyl chain ends,
*$^1$H NMR,
IBCE = isobutyl chain end.

TABLE 3A

GPC-DRI(PP standard)

| | | $^1$H NMR | GPC-DRI (PP Std) | | |
|---|---|---|---|---|---|
| Ex. | $H_2$, psi | $M_N$ | $M_N$ | $M_W$ | $M_Z$ |
| 2 | 0 | 4516 | 3245 | 9600 | 21306 |
| 4 | 0 | 3617 | 3262 | 9584 | 22496 |
| 5 | 0 | 1017 | 576 | 2745 | 12604 |
| 13 | 0 | 1133 | 811 | 7546 | 675,306 |
| 24 | 0 | 1934 | 360 | 12,359 | 614,945 |
| 33 | 0 | 1283 | 947 | 3,703 | 10,279 |
| 35 | 0 | 4546 | 4,080 | 19,065 | 313,648 |
| 36 | 0 | 2863 | 2,075 | 13,793 | 1,541,001 |
| 42 | 0 | 4473 | 3,410 | 26,362 | 180,129 |
| 45 | 0 | 1013.02 | 504 | 2,409 | 9,196 |
| 63 | 0 | 945 | 468 | 1,736 | 4,143 |
| 64 | 7 | 275 | 106 | 265 | 611 |
| 65 | 7 | 570 | 255 | 850 | 1,883 |
| 66 | 7 | 838 | 389 | 1,810 | 4,557 |
| 67 | 7 | 261 | 98 | 198 | 431 |
| 68 | 7 | 433 | 183 | 538 | 1,142 |
| 71 | 7 | 285.4 | 134 | 395 | 1,676 |
| 72 | 50 | 315.7 | 153 | 443 | 1,600 |
| 73 | 7 | 443.5 | 102 | 288 | 1,143 |
| 74 | 22 | 380.8 | 156 | 564 | 1,440 |
| 52 | 0 | 773 | 378 | 2,277 | 22,624 |
| 53 | 0 | 929 | 466 | 9,804 | 53,617 |
| 54 | 0 | 795 | 315 | 3,577 | 38,176 |
| 55 | 0 | 974 | 651 | 3,290 | 23,906 |
| 56 | 0 | 490 | 294 | 1,292 | 9,395 |
| 57 | 0 | 112 | 490 | 5,208 | 31,162 |
| 58 | 0 | 1071 | 501 | 6,709 | 65,024 |
| 59 | 0 | 1580 | 633 | 11,053 | 118,559 |
| 60 | 0 | 4861 | 3,519 | 71,123 | 433,478 |
| 61 | 0 | 1877 | 900 | 16,764 | 348,185 |

TABLE 4

Properties of Propylene-Ethylene Copolymers

| Sample | Mole fraction propylene in product* | Wt fraction propylene in product* | Tg (° C.) | % vinyls* | DP* | Mn* |
|---|---|---|---|---|---|---|
| 33 | — | — | −45.6 | 82.5 | 30.6 | 1283 |
| 35 | 0.555 | 0.652 | −53.1 | 84.1 | 108.2 | 4545 |
| 52 | 0.629 | 0.718 | −88 | 95.9 | 18.4 | 773 |
| 53 | 0.447 | 0.578 |  | 97.2 | 22.1 | 929 |
| 54 | 0.501 | 0.606 |  | 96.4 | 18.9 | 795 |
| 55 | 0.428 | 0.529 | −83 | 95.9 | 23.2 | 974 |
| 56 | 0.611 | 0.702 |  | 94.6 | 11.7 | 490 |
| 57 | 0.434 | 0.535 |  | 94.9 | 26.8 | 1124 |
| 58 | 0.378 | 0.472 |  | 94.8 | 25.5 | 1071 |
| 59 | 0.351 | 0.447 |  | 96.5 | 37.6 | 1580 |
| 60 | 0.124 | 0.176 |  | 76.4 | 115.7 | 4861 |
| 61 | 0.247 | 0.329 |  | 99.1 | 44.7 | 1877 |

*Calculated from $^1$H NMR % Vinyls = % allyl chain ends

Examples 35 and 52-61 were characterized by $^{13}$C NMR as described above then compared to the data in *Macromolecules* 2008 41, 559-567.

TABLE 5

Allyl chain ends in Propylene-Ethylene Co-oligomers

| Source | Wt % ethylene | Mol % ethylene | % allyl chain ends |
|---|---|---|---|
| M-Tab 1† | 0.0 | 0.00 | 100 |
| M-Tab 1† | 21.4 | 29.0 | 65.0 |
| M-Tab 1† | 29.9 | 39.0 | 60.0 |
| M-Tab 1† | 51.0 | 61.0 | 43.0 |
| Coates Tab 1† | 54.2 | 64.0 | 42.0 |
| 35 | 34.8 | 44.5 | 84.1 |
| 52 | 28.2 | 37.1 | 95.9 |
| 53 | 42.2 | 55.3 | 97.2 |
| 54 | 39.4 | 49.9 | 96.4 |
| 55 | 47.1 | 57.2 | 95.9 |
| 56 | 29.8 | 38.9 | 94.6 |
| 57 | 46.5 | 56.6 | 94.9 |
| 58 | 52.8 | 62.2 | 94.8 |
| 59 | 55.3 | 64.9 | 96.5 |
| 60* | 82.4 | 87.6 | 76.4* |
| 61 | 67.1 | 75.3 | 99.1 |

M-Tab is table 1 of † *Macromolecules* 2008 41, 559-567
*10C exotherm

TABLE 6 percent Chain End Microstructures from $^{13}$C NMR

| Sample | Saturated End Groups* | | Unsaturated End Groups | | Init/Term |
|---|---|---|---|---|---|
|  | IB-P | IB-E | Vinyl-P | Vinyl-E |  |
| 52 | 71.8 | 28.2 | 71.7 | 28.3 | 1.31 |
| 53 | 64.5 | 35.5 | 64.1 | 35.9 | 1.32 |
| 55 | 48.6 | 51.4 | 61.8 | 38.2 | 1.16 |
| 56 | 62.4 | 37.6 | 65.6 | 34.4 | 1.03 |

Saturated chain end microstructure analysis reveals the surprising result that propylene is nearly always the first monomer inserted following β-Methyl elimination or transfer involving a growing chain and/or incoming monomer, even in polymers containing up to 52 mole % ethylene.

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law.

What is claimed is:

1. A homogenous process for making a propylene co-oligomer, said process having productivity of at least 4500 g/mmol/hr, wherein the process comprises:
contacting, at a temperature of from 35° C. to 150° C., propylene, 0.1 to 70 mol % ethylene and from 0 to about 5 wt % hydrogen in the presence of a catalyst system comprising an activator and at least one metallocene compound represented by at least one of the formulae:
where:

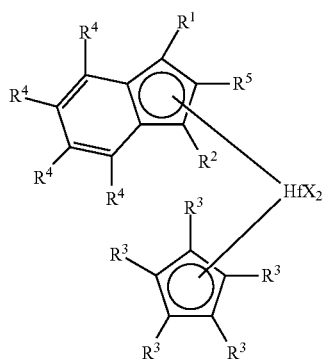

I

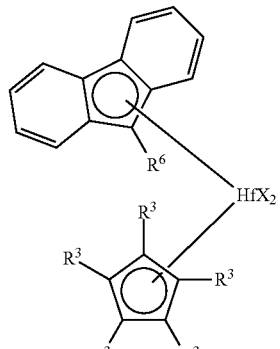

II

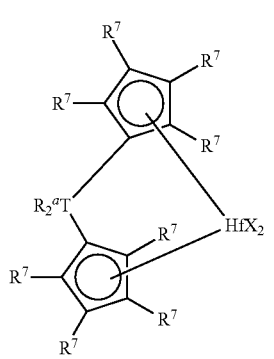

III

-continued

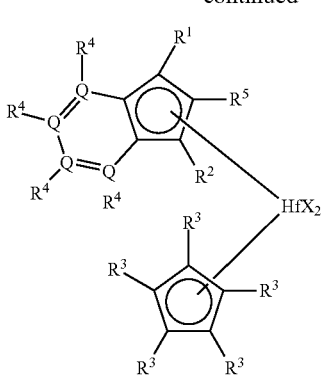

IV

Hf is hafnium;
each X is, independently, selected from the group consisting of hydrocarbyl radicals having from 1 to 20 carbon atoms, hydrides, amides, alkoxides, sulfides, phosphides, halogens, dienes, amines, phosphines, ethers, and a combination thereof, (two X's may form a part of a fused ring or a ring system;
each Q is, independently carbon or a heteroatom;
each $R^1$ is, independently, a $C_1$ to $C_8$ alkyl group, $R^1$ may the same or different as $R^2$;
each $R^2$ is, independently, a $C_1$ to $C_8$ alkyl group;
each $R^3$ is, independently, hydrogen, or a substituted or unsubstituted hydrocarbyl group having from 1 to 8 carbon atoms, provided that at least three $R^3$ groups are not hydrogen;
each $R^4$ is, independently, hydrogen or a substituted or unsubstituted hydrocarbyl group, a heteroatom or heteroatom containing group;
$R^5$ is hydrogen or a $C_1$ to $C_8$ alkyl group;
$R^6$ is hydrogen or a $C_1$ to $C_8$ alkyl group;
each $R^7$ is, independently, hydrogen, or a $C_1$ to $C_8$ alkyl group, provided that at least seven $R^7$ groups are not hydrogen;
T is a bridge;
each Ra, is independently, hydrogen, halogen or a $C_1$ to $C_{20}$ hydrocarbyl, and two $R^a$ can form a cyclic structure including aromatic, partially saturated, or saturated cyclic or fused ring system;
and further provided that any two adjacent R groups may form a fused ring or multicenter fused ring system where the rings may be aromatic, partially saturated or saturated.

2. The process of claim 1, wherein the propylene co-oligomer obtained is a co-oligomer having an Mn of 300 to 30,000 g/mol (measured by $^1$H NMR) comprising 10 to 90 mol % propylene and 10 to 90 mol % of ethylene, wherein the oligomer has at least X % allyl chain ends (relative to total unsaturations), where: 1) X=(−0.94*(mole % ethylene incorporated)+100), when 10 to 60 mole % ethylene is present in the co-oligomer, and 2) X=45, when greater than 60 and less than 70 mole % ethylene is present in the co-oligomer, and 3) X=(1.83*(mole % ethylene incorporated)−83), when 70 to 90 mole % ethylene is present in the co-oligomer.

3. The process of claim 2, wherein the propylene co-oligomer has more than 90% allyl chain ends (relative to total unsaturations).

4. The process of claim 2, wherein the propylene co-oligomer comprises from 85 to 15 mol % ethylene and has more than 80% allyl chain ends (relative to total unsaturations).

5. The process of claim 2, wherein the propylene co-oligomer comprises from 20 to 80 mol % ethylene and has more than 70% allyl chain ends (relative to total unsaturations).

6. The process of claim 2, wherein the propylene co-oligomer comprises from 25 to 70 mol % ethylene and has more than 90% allyl chain ends (relative to total unsaturations).

7. The process of claim 2, wherein the propylene co-oligomer is a liquid at 25° C.

8. The process of claim 2, wherein the Mn is about 500 to about 7,500 g/mol, the Mw is 1,000 to about 20,000 g/mol, and the Mz is about 1400 to about 150,000 g/mol.

9. The process of claim 1, wherein the propylene co-oligomer obtained is a propylene co-oligomer comprising more than 90 mol % propylene and less than 10 mol % ethylene wherein the co-oligomer has: at least 93% allyl chain ends, a number average molecular weight (Mn) of about 500 to about 20,000 g/mol, an isobutyl chain end to allylic vinyl group ratio of 0.8:1 to 1.35:1.0, and less than 100 ppm aluminum.

10. The process of claim 9, wherein the propylene co-oligomer is a liquid at 25° C.

11. The process of claim 1, wherein the propylene co-oligomer obtained is a propylene co-oligomer comprising: at least 50 mol % propylene and from 10 to 50 mol % ethylene, wherein the co-oligomer has: at least 90% allyl chain ends, an Mn of about 150 to about 10,000 g/mol, and an isobutyl chain end to allylic vinyl group ratio of 0.8:1 to 1.2:1.0, wherein monomers having four or more carbon atoms are present at from 0 to 3 mol %.

12. The process of claim 1, wherein the propylene co-oligomer obtained is a propylene co-oligomer comprising: at least 50 mol % propylene, from 0.1 to 45 mol % ethylene, and from 0.1 to 5 mol % $C_4$ to $C_{12}$ olefin, wherein the oligomer has: at least 90% allyl chain ends, an Mn of about 150 to about 10,000 g/mol, and an isobutyl chain end to allylic vinyl group ratio of 0.8:1 to 1.35:1.0.

13. The process of claim 1, wherein the propylene co-oligomer obtained is a propylene co-oligomer comprising: at least 50 mol % propylene, from 0.1 to 45 wt % ethylene, and from 0.1 to 5 mol % diene, wherein the oligomer has: at least 90% allyl chain ends, an Mn of about 150 to about 10,000 g/mol, and an isobutyl chain end to allylic vinyl group ratio of 0.7:1 to 1.35:1.0.

14. The process of claim 1, wherein the activator comprises one or more non-coordinating anions.

15. The process of claim 1, wherein the catalyst system comprises one or more of (pentamethylcyclopentadienyl)(1,3 dimethylindenyl) hafnium dimethyl, and (pentamethylcyclopentadienyl)(1,3 dimethylindenyl) hafnium) dichloride.

16. The process of claim 1, wherein the catalyst system comprises one or more of
(1,3-dimethylindenyl)(pentamethylcyclopentadienyl) hafnium dimethyl,
(1,3,4,7-tetramethylindenyl)(pentamethylcyclopentadienyl) hafnium dimethyl,
(1,3-dimethylindenyl)(tetramethylcyclopentadienyl) hafnium dimethyl,
(1,3-diethylindenyl)(pentamethylcyclopentadienyl) hafnium dimethyl,
(1,3-dipropylindenyl)(pentamethylcyclopentadienyl) hafnium dimethyl,
(1-methyl,3-propyllindenyl)(pentamethylcyclopentadienyl) hafnium dimethyl,
(1,3-dimethylindenyl)(tetramethylpropylcyclopentadienyl) hafnium dimethyl,
(1,2,3-trimethylindenyl)(pentamethylcyclopentadienyl) hafnium dimethyl, (1,3-dimethylbenzindenyl)(pentamethylcyclopentadienyl) hafnium dimethyl,
(9-methylfluorenyl)(pentamethylcyclopentadienyl) hafnium dimethyl,
μ-dihydrosilyl(bis-tetramethylcyclopentadienyl) hafnium dimethyl,
μ-dimethylsilyl(tetramethylcyclopentadienyl)(3-propyltrimethylcyclopentadienyl) hafnium dimethyl,
μ-dicyclopropylsilyl(bis-tetramethylcyclopentadienyl) hafnium dimethyl,
(1,3-dimethylindenyl)(pentamethylcyclopentadienyl) hafnium dihalide,
(1,3,4,7-tetramethylindenyl)(pentamethylcyclopentadienyl) hafnium dihalide,
(1,3-dimethylindenyl)(tetramethylcyclopentadienyl) hafnium dihalide,
(1,3-diethylindenyl)(pentamethylcyclopentadienyl) hafnium dihalide,
(1,3-dipropylindenyl)(pentamethylcyclopentadienyl) hafnium dihalide,
(1-methyl,3-propyllindenyl)(pentamethylcyclopentadienyl) hafnium dihalide,
(1,3-dimethylindenyl)(tetramethylpropylcyclopentadienyl) hafnium dihalide,
(1,2,3-trimethylindenyl)(pentamethylcyclopentadienyl) hafnium dihalide,
(1,3-dimethylbenzindenyl)(pentamethylcyclopentadienyl) hafnium dihalide,
(9-methylfluorenyl)(pentamethylcyclopentadienyl) hafnium dihalide,
μ-dihydrosilyl(bis-tetramethylcyclopentadienyl) hafnium dihalide,
μ-dihydrosilyl(bis-tetramethylcyclopentadienyl) hafnium dihalide,
μ-dimethylsilyl(tetramethylcyclopentadienyl)(3-propyltrimethylcyclopentadienyl) hafnium dihalide, and
μ-dicyclopropylsilyl(bis-tetramethylcyclopentadienyl) hafnium dihalide.

17. The process of claim 1, further comprising functionalizing the propylene co-oligomer.

18. The process of claim 1, further comprising functionalizing the propylene co-oligomer with succinic acid, maleic acid, maleic anhydride or combinations thereof.

19. The process of claim 1, wherein the propylene co-oligomer has an isobutyl chain end to allylic chain end ratio of 0.9:1 to 1.1:1.0.

20. The process of claim 1, wherein the propylene co-oligomer has an Mw/Mn by GPC-DRI of 1.5 to 20 and an isobutyl chain end to allylic vinyl group ratio of 0.8:1 to 1.35:1.0.

21. The process of claim 1, wherein the Mw/Mn is 1.7 to 10.

22. The process of claim 1, wherein the propylene co-oligomer has a number average molecular weight (Mn) of about 600 to about 15,000 g/mol.

23. The process of claim 1, wherein X is 95%.

24. The process of claim 1, wherein the propylene co-oligomer has an Mn of about 400 to about 10,000 g/mol.

25. The process of claim 1, wherein the propylene co-oligomer has an Mn of 300 to 30,000 g/mol (measured by $^1$H NMR) and comprises 10 to 50 mol % propylene and 50 to 90 mol % of ethylene, wherein the propylene co-oligomer has at least X % allyl chain ends (relative to total unsaturations), where: 1) X=(1.20(−0.94*(mole % ethylene incorporated)+100)), when 50 to 60 mole % ethylene is present in the propylene co-oligomer, and 2) X=50, when greater than 60 and less than 70 mole % ethylene is present in the propylene co-oligomer, and 3) X=(1.20(1.83*(mole % ethylene incorporated) −83)), when 70 to 90 mole % ethylene is present in the prop co-oligomer.

26. The process of claim 1, wherein the propylene co-oligomer has an Mn of 300 to 30,000 g/mol (measured by $^1$H NMR) and comprises 10 to 50 mol % propylene and 50 to 90 mol % of ethylene, wherein the propylene co-oligomer has at least X % allyl chain ends (relative to total unsaturations), where: 1) X=(1.50(−0.94*(mole % ethylene incorporated)+100)), when 50 to 60 mole % ethylene is present in the propylene co-oligomer, and 2) X=60, when greater than 60 and less than 70 mole % ethylene is present in the propylene co-oligomer, and 3) X=(1.50(1.83*(mole % ethylene incorporated)−83)), when 70 to 90 mole % ethylene is present in the propylene co-oligomer.

27. The process of claim 1, wherein the propylene co-oligomer has at least 80% isobutyl chain ends.

28. The process of claim 1, wherein the propylene co-oligomer has an isobutyl chain end to allylic chain end ratio of 0.8:1 to 1.35:1.0.

29. The process of claim 1, wherein the propylene co-oligomer has an isobutyl chain end to allylic chain end ratio of 0.9:1 to 1.2:1.0.

30. The process of claim 1, wherein the propylene co-oligomer has been functionalized by reacting a heteroatom containing group with the propylene co-oligomer, with or without catalyst.

31. The process of claim 30, wherein the heteroatom containing group is an amine, an aldehyde, an alcohol, or an acid.

32. The process of claim 30, wherein the heteroatom containing group is succinic acid, maleic acid or maleic anhydride.

33. The process of claim 1, wherein the propylene co-oligomer has a Tg of 0° C. or less.

34. The process of claim 1, wherein the propylene co-oligomer has a melting point of from 60 to 130° C.

35. The process of claim 1, wherein the propylene co-oligomer has no dectectable melting point by DSC following storage at 23° C. for 48 hours.

36. A homogenous process for making a propylene homo-oligomer, said process having productivity of at least 4500 g/mmol/hour, wherein the process comprises:
contacting, at a temperature of from 30° C. to 120° C., propylene, 0 mol % comonomer and from 0 to about 5 wt % hydrogen in the presence of a catalyst system comprising an activator and at least one metallocene compound represented by the formulae:
where

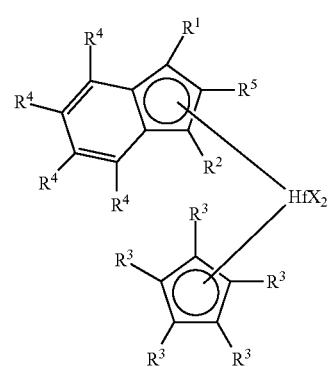

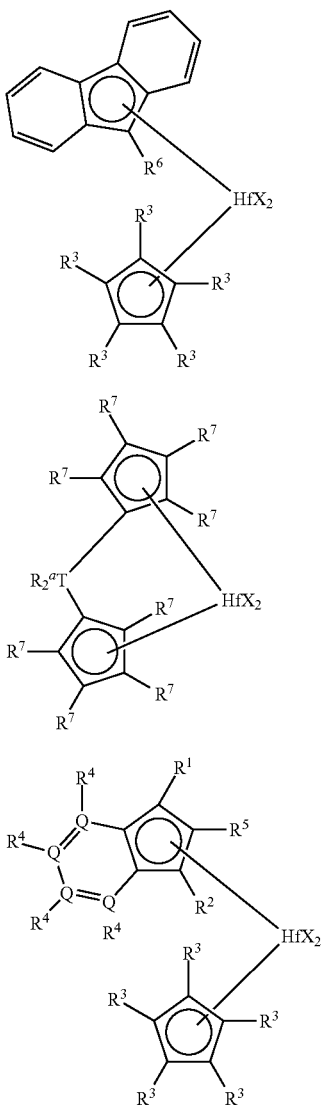

Hf is hafnium;
each X is, independently, selected from the group consisting of hydrocarbyl radicals having from 1 to 20 carbon atoms, hydrides, amides, alkoxides, sulfides, phosphides, halogens, dienes, amines, phosphines, ethers, and a combination thereof, (two X's may form a part of a fused ring or a ring system;
each Q is, independently carbon or a heteroatom;
each $R^1$ is, independently, a $C_1$ to $C_8$ alkyl group, $R^1$ may the same or different as $R^2$;
each $R^2$ is, independently, a $C_1$ to $C_8$ alkyl group;
each $R^3$ is, independently, hydrogen, or a substituted or unsubstituted hydrocarbyl group having from 1 to 8 carbon atoms, provided that: 1) all five $R^3$ groups are methyl, or 2) four $R^3$ groups are not hydrogen and at least one $R^3$ group is a $C_2$ to $C_8$ substituted or unsubstituted hydrocarbyl;
each $R^4$ is, independently, hydrogen or a substituted or unsubstituted hydrocarbyl group, a heteroatom or heteroatom containing group;
$R^5$ is hydrogen or a $C_1$ to $C_8$ alkyl group;
$R^6$ is hydrogen or a $C_1$ to $C_8$ alkyl group;
each $R^7$ is, independently, hydrogen, or a $C_1$ to $C_8$ alkyl group, provided that at least seven $R^7$ groups are not hydrogen;
T is a bridge;
each Ra, is independently, hydrogen, halogen or a $C_1$ to $C_{20}$ hydrocarbyl, and two Ra can form a cyclic structure including aromatic, partially saturated, or saturated cyclic or fused ring system;
and further provided that any two adjacent R groups may form a fused ring or multicenter fused ring system where the rings may be aromatic, partially saturated or saturated.

37. The process of claim 36, wherein the propylene oligomer obtained is a homo-oligomer, comprising propylene, wherein the homo-oligomer has: at least 93% allyl chain ends, an Mn of about 500 to about 20,000 g/mol, an isobutyl chain end to allylic vinyl group ratio of 0.8:1 to 1.2:1.0, and less than 1400 ppm aluminum.

38. The homo-oligomer of claim 37, wherein the propylene homo-oligomer is a liquid at 25° C.

39. The process of claim 36, wherein the activator comprises one or more non-coordinating anions.

40. The process of claim 36, wherein the catalyst system comprises one or more of
(1,3-dimethylindenyl)(pentamethylcyclopentadienyl) hafnium dimethyl,
(1,3,4,7-tetramethylindenyl)(pentamethylcyclopentadienyl) hafnium dimethyl,
(1,3-diethylindenyl)(pentamethylcyclopentadienyl) hafnium dimethyl,
(1,3-dipropylindenyl)(pentamethylcyclopentadienyl) hafnium dimethyl,
(1-methyl,3-propyllindenyl)(pentamethylcyclopentadienyl) hafnium dimethyl,
(1,2,3-trimethylindenyl)(pentamethylcyclopentadienyl) hafnium dimethyl,
(1,3-dimethylbenzindenyl)(pentamethylcyclopentadienyl) hafnium dimethyl,
(9-methylfluorenyl)(pentamethylcyclopentadienyl) hafnium dimethyl,
(1,3-dimethylindenyl)(pentamethylcyclopentadienyl) hafnium dihalide,
(1,3,4,7-tetramethylindenyl)(pentamethylcyclopentadienyl) hafnium dihalide,
(1,3-diethylindenyl)(pentamethylcyclopentadienyl) hafnium dihalide,
(1,3-dipropylindenyl)(pentamethylcyclopentadienyl) hafnium dihalide,
(1-methyl-3-propyllindenyl)(pentamethylcyclopentadienyl) hafnium dihalide,
(1,2,3-trimethylindenyl)(pentamethylcyclopentadienyl) hafnium dihalide,
(1,3-dimethylbenzindenyl)(pentamethylcyclopentadienyl) hafnium dihalide, and.

41. The process of claim 36, further comprising functionalizing the propylene homo-oligomer.

42. The process of claim 36, wherein the propylene homo-oligomer has a Tg of 0° C. or less.

43. The process of claim 36, wherein the propylene homo-oligomer has a melting point of from 60 to 130° C.

44. The process of claim 36, wherein the propylene homo-oligomer has no detectable melting point by DSC following storage at 23° C. for 48 hours.

45. The process of claim 36, wherein the propylene homo-oligomer comprises propylene and 0 wt % comonomer, and has: at least 95% allyl chain ends, an Mn of about 700 to about 10,000 g/mol, an isobutyl chain end to allylic vinyl group ratio of 0.8:1 to 1.2:1.0, and less than 1400 ppm aluminum.

46. The process of claim 36, wherein the propylene homo-oligomer comprises propylene and 0 wt % comonomer, and has: at least 98% allyl chain ends, an Mn of about 500 to about 20,000 g/mol, an isobutyl chain end to allylic vinyl group ratio of 0.8:1 to 1.2:1.0, and less than 1400 ppm aluminum.

47. The process of claim 36, wherein the propylene homo-oligomer comprises propylene and has: at least 95% allyl chain ends, an Mn of about 500 to about 20,000 g/mol, an isobutyl chain end to allylic vinyl group ratio of 0.8:1 to 1.2:1.0, less than 1400 ppm aluminum, and an Mw/Mn by GPC-DRI of 1.5 to 20.

48. The process of claim 47, wherein the Mw/Mn is 1.7 to 20.

49. The process of claim 47, wherein the Mw/Mn is 1.7 to 10.

* * * * *